US012727941B2

(12) United States Patent
Gundert et al.

(10) Patent No.: US 12,727,941 B2
(45) Date of Patent: Sep. 8, 2026

(54) TISSUE MODIFICATION SYSTEMS AND METHODS AND SIGNAL GENERATORS FOR USE THEREWITH

(71) Applicant: Galary, Inc., San Carlos, CA (US)

(72) Inventors: Timothy J. Gundert, Discovery Bay, CA (US); Robert E. Neal, II, Redwood City, CA (US); Quim Castellvi, Barcelona (ES); David W. Hunter, Catonsville, MD (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 974 days.

(21) Appl. No.: 17/587,844

(22) Filed: Jan. 28, 2022

(65) Prior Publication Data

US 2023/0240746 A1 Aug. 3, 2023

(51) Int. Cl.
*A61B 18/12* (2006.01)
*A61B 18/16* (2006.01)
*A61B 18/00* (2006.01)

(52) U.S. Cl.
CPC .......... *A61B 18/16* (2013.01); *A61B 18/1206* (2013.01); *A61B 2018/0072* (2013.01); (Continued)

(58) Field of Classification Search
CPC ................ A61B 18/16; A61B 18/1206; A61B 2018/0072; A61B 2018/00755; (Continued)

(56) References Cited

U.S. PATENT DOCUMENTS 6,241,751 B1 6/2001 Morgan et al.
9,987,081 B1 6/2018 Bowers et al.
(Continued)

FOREIGN PATENT DOCUMENTS

CN 113558744 A 10/2021
WO WO2016/061002 A1 4/2016
(Continued)

OTHER PUBLICATIONS

International Preliminary Report on Patentability dated Aug. 8, 2024, International Application No. PCT/US2023060897.
(Continued)

*Primary Examiner* — Beverly M Flanagan
*Assistant Examiner* — Abigail M Ziegler
(74) *Attorney, Agent, or Firm* — Pearl Cohen LLP

(57) ABSTRACT

Tissue treatment systems and methods are disclosed. In an embodiment, a tissue treatment system includes a LV signal generator, a HV signal generator, and a controller. The LV signal generator is used to produce a LV tissue impedance measurement signal, and the HV signal generator is used to produce a HV tissue treatment signal having a voltage that is at least five times greater than a voltage of the LV tissue impedance measurement signal. The controller controls when the HV tissue treatment signal produced using the HV signal generator, and when the LV tissue impedance measurement signal produced using the LV signal generator, are delivered to patient tissue via an active electrode and a return electrode. The LV tissue impedance measurement signal is used to estimate the impedance of the patient tissue, which is used to control the voltage and/or current of the HV tissue treatment signal.

17 Claims, 9 Drawing Sheets

(52) U.S. Cl.
CPC ............... *A61B 2018/00755* (2013.01); *A61B 2018/00827* (2013.01); *A61B 2018/00875* (2013.01)

(58) Field of Classification Search
CPC ........... A61B 2018/00827; A61B 2018/00875; A61B 2018/00577; A61B 2018/00613
See application file for complete search history.

(56) References Cited

U.S. PATENT DOCUMENTS

| | | | | |
|---|---|---|---|---|
| 10,016,232 | B1 | 7/2018 | Bowers et al. | |
| 10,322,286 | B2 | 6/2019 | Viswanathan et al. | |
| 10,694,972 | B2 | 6/2020 | Davalos et al. | |
| 11,903,690 | B2 | 2/2024 | Davalos et al. | |
| 2010/0023004 | A1 | 1/2010 | Francischelli et al. | |
| 2015/0066108 | A1 | 3/2015 | Shi et al. | |
| 2015/0112321 | A1* | 4/2015 | Cadouri | A61B 18/1206 606/34 |
| 2016/0022349 | A1* | 1/2016 | Woloszko | A61B 18/14 606/34 |
| 2016/0074091 | A1* | 3/2016 | Amoah | A61B 18/1206 606/34 |
| 2017/0360326 | A1 | 12/2017 | Davalos et al. | |
| 2019/0126037 | A1 | 5/2019 | Sarnago et al. | |
| 2019/0247647 | A1 | 8/2019 | Samejima et al. | |
| 2020/0222114 | A1* | 7/2020 | Johnson | A61B 18/1492 |
| 2020/0260987 | A1 | 8/2020 | Davalos et al. | |
| 2021/0022794 | A1 | 1/2021 | Viswanathan | |
| 2021/0038280 | A1* | 2/2021 | Pikramenos | A61B 34/25 |
| 2021/0137410 | A1 | 5/2021 | O'Brien et al. | |
| 2021/0228260 | A1* | 7/2021 | Canady, Jr. | A61B 18/1206 |
| 2021/0393327 | A1 | 12/2021 | Eyster et al. | |
| 2022/0233237 | A1* | 7/2022 | Adams | A61B 18/1492 |
| 2022/0249157 | A1* | 8/2022 | Viswanathan | A61B 18/1206 |
| 2023/0165629 | A1* | 6/2023 | Tehrani | A61B 18/1477 606/34 |
| 2024/0277245 | A1 | 8/2024 | Davalos et al. | |

FOREIGN PATENT DOCUMENTS

| | | | |
|---|---|---|---|
| WO | WO2016/100325 | A1 | 6/2016 |
| WO | WO2019/133606 | A1 | 7/2019 |
| WO | WO2019/157359 | A1 | 8/2019 |

OTHER PUBLICATIONS

Invitation to Pay Additional Fees dated May 15, 2023, International Application No. PCT/US2023060897.
Response to Rule 161(1) and 162 Communication dated Feb. 26, 2025, European Patent Application No. 23706231.0.
Examination Report dated Mar. 11, 2025, Australian Patent Application No. 2023213873.
Communication under Rule 71(3) EPC dated May 16, 2025, European Patent Application No. 23706231.0.
Response to Examiner's Report dated Jun. 3, 2025, Australian Patent Application No. 2023213873.
Notification of Reasons for Rejections dated Jul. 8, 2025, Japanese Patent Application No. 2024-544877.
Notice of Acceptance for patent application dated Jul. 3, 2025, Australian Patent Application No. 2023213873.
Office Action dated Jul. 7, 2025, Canadian Patent Application No. 3,248,836.
Response to Office Action dated Aug. 25, 2025, Canadian Patent Application No. 3,248,836.
Communication under Rule 71(3) EPC dated Sep. 12, 2025, EP Patent Application No. 23706231.0-1122.
Notification of Reasons for Rejections dated Nov. 25, 2025, Japanese Patent Application No. 2024-544877.
Response to Notice of Reasons for Rejections and English translation of Claims amendment dated Feb. 24, 2026, Japanese Patent Application No. 2024-544877.
International Search Report & The Written Opinion of the International Searching Authority dated Jul. 7, 2023, International Application No. PCT/US2023060897.
Notice of Reason for Rejection dated Apr. 28, 2026, Japanese Patent Application No. 2024-544877.
Office Action dated Apr. 14, 2026, Canadian Patent Application No. 3,248,836.

* cited by examiner

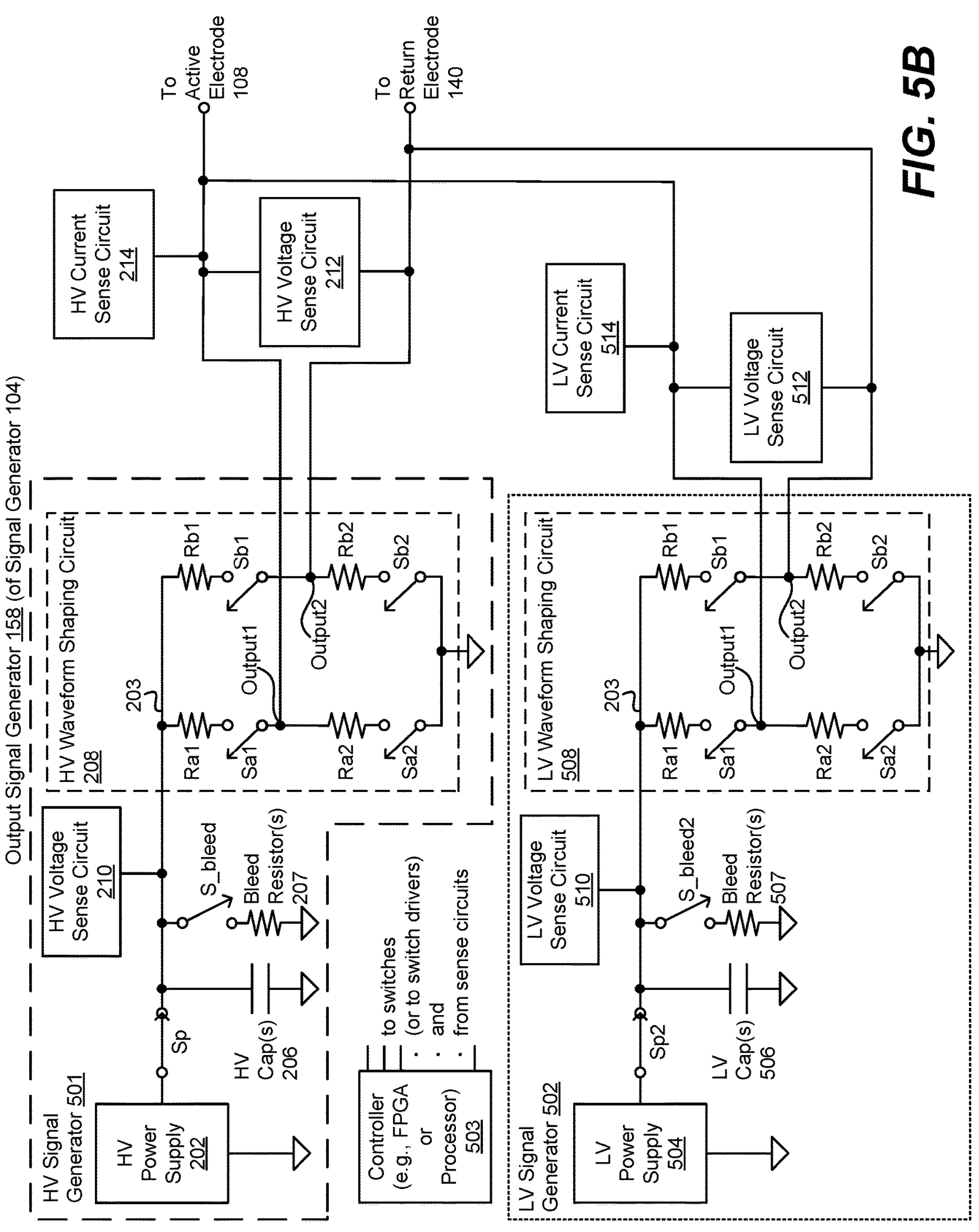
To Active Electrode 108
To Return Electrode 140
FIG. 5B
HV Current Sense Circuit 214
HV Voltage Sense Circuit 212
LV Current Sense Circuit 514
LV Voltage Sense Circuit 512
Output Signal Generator 158 (of Signal Generator 104)
HV Waveform Shaping Circuit 208
203
Rb1
Sb1
Rb2
Sb2
Output1
Output2
Ra1
Sa1
Ra2
Sa2
HV Voltage Sense Circuit 210
S_bleed
Bleed Resistor(s) 207
HV Signal Generator 501
HV Power Supply 202
Sp
HV Cap(s) 206
Controller (e.g., FPGA or Processor) 503
to switches (or to switch drivers) and from sense circuits
LV Waveform Shaping Circuit 508
LV Voltage Sense Circuit 510
S_bleed2
Bleed Resistor(s) 507
LV Signal Generator 502
LV Power Supply 504
Sp2
LV Cap(s) 506

TISSUE MODIFICATION SYSTEMS AND METHODS AND SIGNAL GENERATORS FOR USE THEREWITH

FIELD OF TECHNOLOGY

Certain embodiments of the present technology relate to signal generators for use in a treatment system, such as a tissue modification system, and to treatment systems that include a signal generator. Certain embodiments of the present technology also relate to methods for use by and/or with signal generators and/or by treatment systems that include a signal generator.

BACKGROUND

Pulsed electric field therapy (PEF) can be used to deliver high voltage, short duration pulses to affect diseased tissue in a variety of endoluminal structures (airways, gastrointestinal tract), unresectable tissue targets (liver, pancreas, lungs, kidneys), or cancerous solid tumors. However, delivering PEF therapy with delivered voltage as the targeted therapeutic metric may result in significant differences in patient outcomes. This is due at least in part because of patient-to-patient variability, as well as session-to-session variability, where a session constitutes a period of time that a patient is treated under generally consistent exogenous factors. Session-session variability may therefore include different patients or different patient conditions. Patient-to-patient variability and session-to-session variability can result from differences in numerous factors, including hydration, gender, blood pressure, dispersive electrode pad placement, skin thickness, hair at the site of the dispersive electrode, materials delivered locally or systemically to the patient, and many other factors. It would be beneficial if PEF treatments, and more generally, HV tissue treatments could be controlled to account for both patient-to-patient variability, as well as session-to-session variability.

SUMMARY

Tissue treatment systems and methods are disclosed herein, which can be used to deliver HV tissue treatment signals in a manner that accounts for both patient-to-patient variability, as well as session-to-session variability.

In certain embodiments, a tissue treatment system includes a LV signal generator, a HV signal generator, and a controller. The LV signal generator is used to produce a LV tissue impedance measurement signal, and the HV signal generator is used to produce a HV tissue treatment signal having a voltage that is at least five times greater than a voltage of the LV tissue impedance measurement signal. The controller controls when the HV tissue treatment signal produced using the HV signal generator, and when the LV tissue impedance measurement signal produced using the LV signal generator, are delivered to patient tissue via an active electrode and a return electrode. The LV tissue impedance measurement signal is used to estimate the impedance of the patient tissue, which is used to control the voltage and/or current of the HV tissue treatment signal.

In accordance with certain embodiments, the tissue treatment signal also includes a current sense circuit configured to measure a current that is delivered to the patient tissue via the active electrode while the LV tissue impedance measurement signal, which is produced using the LV signal generator, is delivered to the patient tissue. In certain such embodiments, the controller is further configured to produce an estimate of an impedance of the patient tissue based on the voltage of the LV tissue impedance measurement signal that is delivered to the patient tissue and based on the current measured by the current sense circuit, and control the voltage of the HV tissue treatment signal, which is produced using the HV signal generator, based on the estimate of the impedance of the patient tissue.

In accordance with certain embodiments, the controller is configured to control the voltage of the HV tissue treatment signal, which is produced using the HV signal generator, based on the estimate of the impedance of the patient tissue, so that the patient tissue is treated with a current that is approximately equal to a predetermined target current when the HV tissue treatment signal is delivered to the patient tissue.

In accordance with certain embodiment, in-between each of a plurality of separate instances of the HV signal generator being used to produce the HV tissue treatment signal that is delivered to the patient tissue, the controller is configured to cause the LV signal generator to be used to produce the LV tissue impedance measurement signal that is delivered to the patient tissue. The controller is also configured to produce an updated estimate of the impedance of the patient tissue based on the voltage of the LV tissue impedance measurement signal that is delivered to the patient tissue and based on an updated measure of the current that is delivered to the patient tissue, as measured using the current sense circuit. The controller is further configured to adjust the voltage of the HV tissue treatment signal that is produced using the HV signal generator, in response to the updated estimate of the impedance of the patient tissue differing from an immediately preceding estimate of the impedance of the patient tissue, so that the patient tissue is treated with a current that is approximately equal to the predetermined target current when the HV tissue treatment signal is next delivered to the patient tissue.

In accordance with certain embodiments, the LV signal generator includes a LV power supply, and the HV signal generator includes a HV power supply that is distinct from the LV power supply of the LV signal generator. In certain such embodiments, the LV signal generator includes a LV waveform shaping circuit coupled between the LV power supply and the active and the return electrodes, and the HV signal generator includes a HV waveform shaping circuit, which is distinct from the LV waveform shaping circuit, and is coupled between the HV power supply and the active and the return electrodes. Alternatively, the LV signal generator and the HV signal generator share a same waveform shaping circuit.

In accordance with certain embodiments, the tissue treatment system further comprises a LV current sense circuit configured to measure a current that is delivered to the patient tissue via the active electrode while the LV tissue impedance measurement signal, which is produced using the LV signal generator, is delivered to the patient tissue. The tissue treatment system can also include a HV current sense circuit, which is distinct from the LV current sense circuit, and is configured to measure a current that is delivered to the patient tissue via the active electrode while the HV tissue treatment signal, which is produced using the HV signal generator, is delivered to the patient tissue. In certain such embodiments, the controller is further configured to produce an estimate of an impedance of the patient tissue based on the voltage of the LV tissue impedance measurement signal that is delivered to the patient tissue and based on the current measured by the LV current sense circuit. The controller is also configured to set a voltage of the HV tissue treatment signal, which is produced using the HV signal generator, based on the estimate of the impedance of the patient tissue. Additionally, the controller is configured to adjust the voltage of the HV tissue treatment signal, which is produced using the HV signal generator, based on the current measured by the HV current sense circuit.

A tissue treatment system, according to certain embodiments, includes a pair of electrodes, a plurality of capacitors, a power supply, a waveform shaping circuit, and a controller. The power supply is configured to charge the plurality of capacitors. The waveform shaping circuit is coupled between the plurality of capacitors and the pair of electrodes. The controller is configured to cause a first subset of the capacitors to be coupled to the waveform shaping circuit during a first period of time during which a LV tissue impedance measurement signal is to be delivered to patient tissue via the pair of electrodes, and cause a second subset of the capacitors to be coupled to the waveform shaping circuit during a second period of time during which a HV tissue treatment signal is to be delivered to the patient tissue via the pair of electrodes. In certain such embodiments, a voltage of the HV tissue treatment signal is at least five times greater than a voltage of the LV tissue impedance measurement signal. The first subset of the capacitors includes at least one of the plurality of capacitors. The second subset of the capacitors includes at least one of the plurality of capacitors and differs from the first subset.

In accordance with certain embodiments, the power supply, the waveform shaping circuit, and the first subset of the capacitors are components of a LV signal generator used to produce the LV tissue impedance measurement signal. The power supply, the waveform shaping circuit, and the second subset of the capacitors are components of a HV signal generator used to produce the HV tissue treatment signal. In such embodiments, the power supply and the waveform shaping circuit are shared by both the LV signal generator and the HV signal generator.

In accordance with certain embodiments, the pair of electrodes include an active electrode and a return electrode, and the tissue treatment system further comprise a current sense circuit configured to measure a current that is delivered to the patient tissue via the active electrode while the LV tissue impedance measurement signal is delivered to the patient tissue. In certain such embodiments, the controller is further configured to produce an estimate of an impedance of the patient tissue based on the voltage of the LV tissue impedance measurement signal that is delivered to the patient tissue and based on the current measured by the current sense circuit. Additionally, the controller is configured to control the voltage of the HV tissue treatment signal based on the estimate of the impedance of the patient tissue.

In accordance with certain embodiments, a method includes: (a) producing a LV tissue impedance measurement signal and delivering the LV tissue impedance measurement signal to patient tissue via an active electrode and a return electrode; (b) measuring a current that is delivered to the patient tissue via the active electrode while the LV tissue impedance measurement signal is delivered to the patient tissue; (c) producing an estimate of an impedance of the patient tissue based on a voltage of the LV tissue impedance measurement signal that is delivered to the patient tissue and based on the current that is measured; and (d) producing a HV tissue treatment signal and delivering the HV tissue treatment signal via the active and return electrodes, wherein a voltage of the HV tissue treatment signal is at least five times greater than the voltage of the LV tissue impedance measurement signal, and wherein the producing the HV tissue treatment signal includes controlling the voltage of the HV tissue treatment signal based on the estimate of the impedance of the patient tissue.

In accordance with certain embodiments, steps (a), (b), (c) and (d) are performed in that order, and after being performed in that order, are repeated in that order such that when step (c) is repeated an updated estimate of the impedance of the patient tissue is produced, and such that when step (d) is repeated the voltage of the HV tissue treatment signal is controlled based on the updated estimate of the impedance of the patient tissue.

In accordance with certain embodiments, steps (a), (b), (c) and (d) are performed in that order, and after being performed in that order, steps (a), (b) and (c) are repeated in that order to produce an updated estimate of the impedance of the patient tissue. In certain such embodiments, the method further comprises determining, based on the updated estimate of the impedance of the patient tissue, whether treatment of the patient tissue was sufficient or whether additional treatment of the patient tissue should be performed at an additional instance of step (d).

In accordance with certain embodiments, when an additional treatment of the patient tissue is to be performed at an additional instance of step (d), then the producing the HV treatment signal at the additional instance of step (d) includes controlling the voltage of the HV tissue treatment signal based on the updated estimate of the impedance of the patient tissue.

In accordance with certain embodiments, the producing the LV tissue impedance measurement signal at step (a) is performed using a LV signal generator, and the producing the HV tissue treatment signal at step (c) is performed using a HV signal generator that is distinct from the LV signal generator.

In accordance with certain embodiments, a method further comprises using a power supply to charge a plurality of capacitors, and using a waveform shaping circuit, coupled between the plurality of capacitors and the active and return electrodes, to shape the LV tissue impedance measurement signal and the HV tissue treatment signal. In certain such embodiments, the producing and the delivering the LV tissue impedance measurement signal at step (a) includes coupling a first subset of the capacitors to the waveform shaping circuit during a first period of time, and the producing and the delivering the HV tissue treatment signal at step (c) includes coupling a second subset of the capacitors to the waveform shaping circuit during a second period of time. The first subset of the capacitors includes at least one of the plurality of capacitors, and the second subset of the capacitors includes at least one of the plurality of capacitors and differs from the first subset.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

FIG. 5B is a high level block diagram of the output signal generator, according to another embodiment of the present technology.

DETAILED DESCRIPTION

Figure 1A:
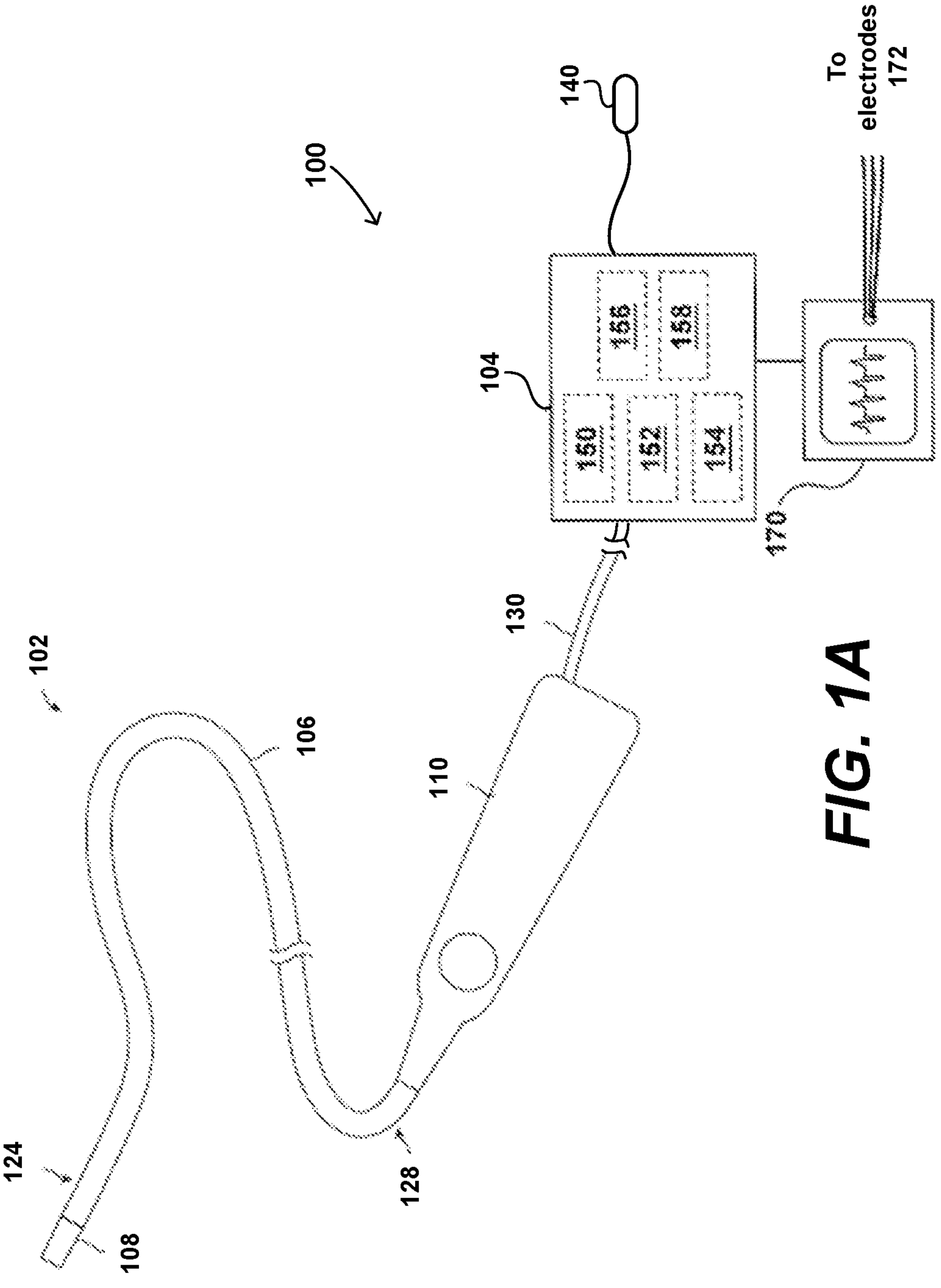
FIG. 1A illustrates an example treatment system used in treatment of a patient.
Figure 1B:
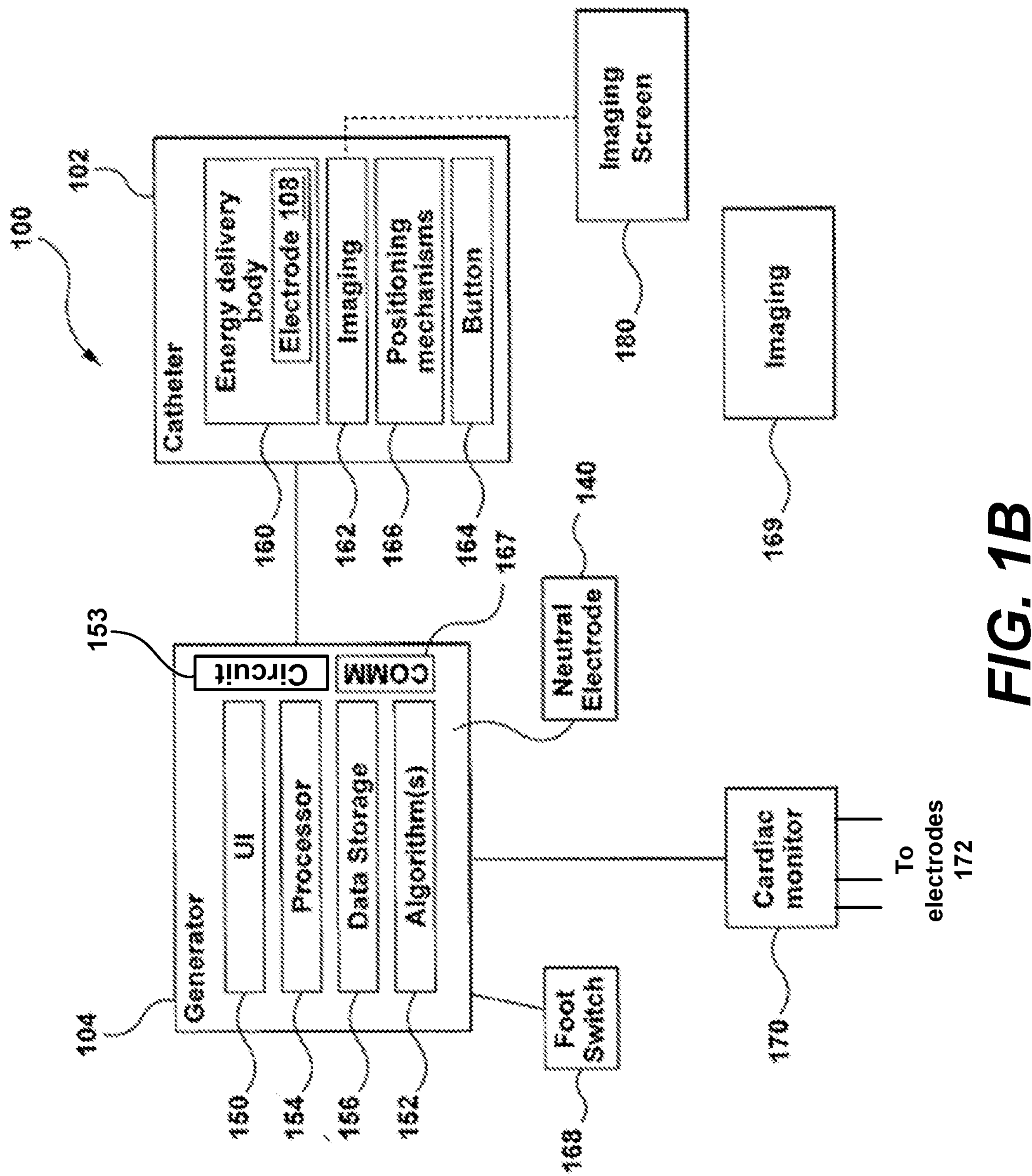
FIG. 1B is a schematic illustration of an embodiment of the treatment system, initially introduced in FIG. 1A.

Certain embodiments of the present relate to signal generators for use in a treatment system, such as a tissue modification system, but not limited thereto. FIG. 1A illustrates an example treatment system 100 used in treatment of a patient. FIG. 1B is a schematic illustration of the embodiment of the treatment system shown in FIG. 1A. In this embodiment, the system 100 comprises a therapeutic energy delivery instrument 102 (e.g., a catheter) connectable to a signal generator 104. The signal generator 104 can be referred to herein more succinctly as the generator 104. Referring to FIG. 1A, the instrument 102 is shown as having an elongate shaft 106 with at least one delivery electrode 108 near its distal end 124 and a handle 110 at its proximal end 128. The instrument 102 is connectable to the generator 104 as part of a treatment system 100. Connection of the instrument 102 to the generator 104 provides electrical energy to the delivery electrode 108, among other features. In this embodiment, the delivery electrode 108 is shown as a "solid tip" electrode having a cylindrical shape with a distal face having a continuous surface. In some embodiments, the cylindrical shape has a diameter across its distal face of approximately 2-3 mm and a length along the shaft 106 of approximately 1 mm, 2 mm, 1-2 mm, 3 mm, 4 mm, 3-4 mm, 5 mm, 6 mm, 7 mm, 8 mm, 9 mm, 10 mm, etc. It may be appreciated that such electrodes are typically hollow yet are referred to as solid due to visual appearance. In some embodiments, the catheter 102 has an overall length of 50-150 cm, preferably 100-125 cm, more preferably 110-115 cm. Likewise, in some embodiments, it has a 7 Fr outer diameter 3-15 Fr, preferably 4-12 Fr, more preferably 7-8.5 Fr. Deflection of the shaft 106 may be achieved by a variety of mechanism including a pull-wire which extends to the handle 110. Thus, the handle 110 is used to manipulate the catheter 102, particularly to steer the distal end during delivery and treatment. Energy is provided to the catheter 102, and therefore to the delivery electrode 108, via a cable 130 that is connectable to the generator 104. In some embodiments, the handle 110 is removable, such as by pressing a handle removal button. The energy delivery electrode 108 can also be referred to herein as the active electrode 108. It may be appreciated that a variety of types of visualization may be used, including angiography (optionally including markers), computed tomography, optical coherence tomography, ultrasound, and direct video visualization, to name a few.

Pulsed electric fields (PEFs) are provided by the generator 104 and delivered to the tissue through the delivery electrode 108 placed on or near the targeted tissue area. It may be appreciated that in some embodiments, the delivery electrode 108 is positioned in contact with a conductive substance which is likewise in contact with the targeted tissue. Such solutions may include isotonic or hypertonic solutions. These solutions may further include adjuvant materials, such as chemotherapy or calcium, to further enhance the treatment effectiveness both for the focal treatment as well as potential regional infiltration regions of the targeted tissue types. High voltage, short duration biphasic electric pulses are then delivered through the electrode 108 in the vicinity of the target tissue. These electric pulses are provided by at least one energy delivery algorithm 152. In some embodiments, each energy delivery algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail below. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

It may be appreciated that in various embodiments the treatment catheter 102 includes a variety of specialized features. For example, in some embodiments, the catheter 102 includes a mechanism for real-time measurement of the contact force applied by the catheter tip to a patient's heart wall during a procedure. In some embodiments, this mechanism is included in the shaft 106 and comprises a tri-axial optical force sensor which utilizes white light interferometry. By monitoring and modifying the applied force throughout the procedure, the user is able to better control the catheter 102 so as to create more consistent and effective lesions. The use of other types of contact force sensors are also possible and within the scope of the embodiments described herein.

In this embodiment, the therapeutic energy delivery instrument 102 is connectable with the generator 104 along with a dispersive electrode 140 applied externally to the skin of a patient. Thus, in this embodiment, monopolar energy delivery is achieved by supplying energy between the energy delivery electrode 108 disposed near the distal end of the instrument 102 and the dispersive electrode 140. The dispersive electrode 140 is also referred to herein as the return electrode 140. It will be appreciated, however, that bipolar energy delivery and other arrangements may alternatively be used. When using bipolar energy delivery, the therapeutic energy delivery instrument 102 may differ in overall design, such as to include a plurality of energy delivery electrodes

108, or may appear similar in overall design, such as to include a single energy delivery electrode 108 which is configured to function in a bipolar manner. In some embodiments, the return electrode 140 is an implanted electrode, located, e.g., on the catheter 102 or a sheath, but not limited thereto. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can spread the treatment effect over a larger, shallower surface area thus requiring a lower voltage to achieve the treatment effect, compared to monopolar. Likewise, this lower voltage may be used to reduce the depth of penetration. In addition, lower voltage requirements may obviate the use of cardiac synchronization in particular cases if the delivered voltage is low enough to avoid capture of the cardiac muscle cells.

In this embodiment, the generator 104 includes a user interface 150, one or more energy delivery algorithms 152, a processor 154, a data storage/retrieval unit 156 (such as a memory and/or database), and an output signal generator circuit 158 which generates and/or stores the energy to be delivered, and produces the desired waveform of the energy to be delivered. In some embodiments, one or more capacitors are used for energy storage/delivery, however any other suitable energy storage element may be used. In some embodiments, various switches are used to generate the desired waveform of the energy to be delivered. In addition, one or more communication ports 167 can be included.

In some embodiments, the generator 104 includes three sub-systems: 1) a high-energy storage system, 2) a high-voltage, medium-frequency switching amplifier, and 3) the system controller, firmware, and user interface. The system controller includes a cardiac synchronization trigger monitor that allows for synchronizing the pulsed energy output to the patient's cardiac rhythm. The generator takes in alternating current (AC) mains to power multiple direct current (DC) power supplies. The generator's controller can cause the DC power supplies to charge a high-energy capacitor storage bank before energy delivery is initiated. At the initiation of therapeutic energy delivery, the generator's controller, high-energy storage banks and a bi-phasic pulse amplifier can operate simultaneously to create a high-voltage, medium frequency output.

It will be appreciated that a multitude of generator electrical architectures may be employed to execute the energy delivery algorithms. In particular, in some embodiments, advanced switching systems are used which are capable of directing the pulsed electric field circuit to the energy delivering electrodes separately from the same energy storage and high voltage delivery system. Further, generators employed in advanced energy delivery algorithms employing rapidly varying pulse parameters (e.g., voltage, frequency, etc.) or multiple energy delivery electrodes may utilize modular energy storage and/or high voltage systems, facilitating highly customizable waveform and geographical pulse delivery paradigms. It should further be appreciated that the electrical architecture described herein above is for example only, and systems delivering pulsed electric fields may or may not include additional switching amplifier components.

The user interface 150 can include a touch screen and/or more traditional buttons to allow for the operator to enter patient data, select a treatment algorithm (e.g., energy delivery algorithm 152), initiate energy delivery, view records stored on the storage/retrieval unit 156, and/or otherwise communicate with the generator 104. The user interface 150 can include a voice-activated mechanism to enter patient data or may be able to communicate with additional equipment in the suite so that control of the generator 104 is through a secondary separate user interface.

In some embodiments, the user interface 150 is configured to receive operator-defined inputs. The operator-defined inputs can include a duration of energy delivery, one or more other timing aspects of the energy delivery pulse, power, and/or mode of operation, or a combination thereof. Example modes of operation can include (but are not limited to): system initiation and self-test, operator input, algorithm selection, pre-treatment system status and feedback, tissue impedance measurement, energy delivery, post energy delivery display or feedback, treatment data review and/or download, software update, or any combination or subcombination thereof. In accordance with certain embodiments, the user interface 150 displays information to a physician or technician, or some other user, during automated therapy delivery where all of the aforementioned dosage parameters (e.g., a duration of energy delivery, one or more other timing aspects of the energy delivery pulse, power, and/or mode of operation, or a combination thereof) can be preset. The user interface 150 can also be used to provide system status following one or more self-tests, and can provide a way for the user to acknowledge system status information. The user interface 150 can also be used to select or otherwise specify a target current and/or target voltage that is to be used for treatment.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104. The cardiac monitor 170 can be used to continuously acquire an ECG signal. External electrodes 172 may be applied to the patient to acquire the ECG. The generator 104 analyzes one or more cardiac cycles and identifies the beginning of a time period during which it is safe to apply energy to the patient, thus providing the ability to synchronize energy delivery with the cardiac cycle. In some embodiments, this time period is within milliseconds of the R wave (of the ECG QRS complex) to avoid induction of an arrhythmia, which could occur if the energy pulse is delivered on a T wave. It will be appreciated that such cardiac synchronization is typically utilized when using monopolar energy delivery, however it may be utilized as part of other energy delivery methods.

In some embodiments, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data, such as related to the treatments delivered, and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

FIG. 1B is a schematic illustration of an embodiment of the treatment system 100, initially introduced in FIG. 1A. In this embodiment, a dispersive (neutral) or return electrode 140 is operatively connected to the generator 104 while affixed to the patient's skin to provide a return path for the energy delivered via the instrument 102. The energy-delivery instrument 102 includes one or more energy delivery electrodes 108, one or more sensors 160, one or more imaging modalities 162, one or more buttons 164, and/or positioning mechanisms 166 (e.g., such as, but not limited to, levers and/or dials on a handle with pull wires, telescoping tubes, a sheath, and/or the like) the one or more energy delivery (active) electrodes 108 into contact with the tissue. In some embodiments, a foot switch 168 is operatively connected to the generator 104 and used to initiate energy delivery. The dispersive electrode 140 can also be referred to herein as the neutral electrode 140, the return electrode 140, or more succinctly as the electrode 140.

As mentioned previously, the user interface 150 can include a touch screen and/or more traditional buttons to allow for the operator to enter patient data, select a treatment algorithm 152, initiate energy delivery, view records stored on the storage/retrieval unit 156, or otherwise communicate with the generator 104. The processor 154 manages and executes the energy-delivery algorithm, monitors the energy delivery and any sensor data, and reacts to monitored data via a feedback loop. The data storage/retrieval unit 156 stores data related to the treatments delivered and can be downloaded by connecting a device (e.g., a laptop or thumb drive) to a communication port 167.

The instrument 102 is operatively connected to the generator 104 and/or a separate imaging screen 180. Imaging modalities 162 can be incorporated into the instrument 102 or used alongside or in conjunction with the instrument 102. Alternatively or in addition, a separate imaging modality or apparatus 169 can be used, such as a commercially-available system (e.g., a bronchoscope). The separate imaging apparatus 169 can be mechanically, operatively, and/or communicatively coupled to the instrument 102 using any suitable mechanism.

Figure 2:
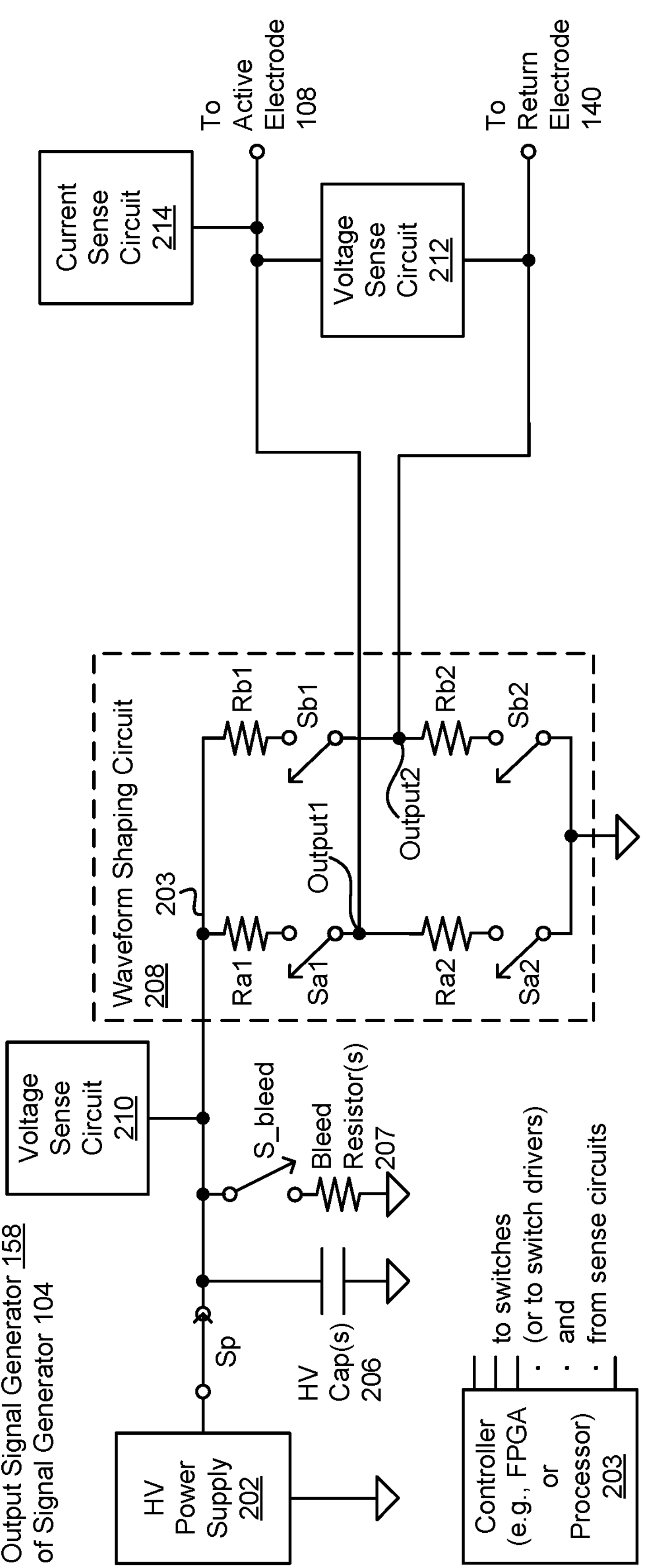
FIG. 2 is an example circuit diagram of an output signal generator circuit of a signal generator introduced in FIGS. 1A and 1B.

FIG. 2 is an example circuit diagram of an embodiment of the output signal generator circuit 158 of the signal generator 104, introduced above in the discussion of FIGS. 1A and 1B. Referring to FIG. 2, the output signal generator circuit 158 is shown as including a high voltage (HV) power supply 202, a controller 203, HV capacitor(s) 206, bleed resistor(s) 207, a waveform shaping circuit 208, a voltage sense circuit 210, a voltage sense circuit 212, and a current sense circuit 214. The output signal generator circuit 158 can include additional circuitry, which is not shown, as would be appreciated by one of ordinary skill in the art. For example, a step-up transformer, a filter, and/or DC blocking capacitors can optionally be coupled between the output nodes (labeled Output 1 and Output 2) of the waveform shaping circuit 208 and the active and return electrodes 108, 140. Such a step-up transformer can be used to step up the voltage signal generated between the output nodes (Output 1 and Output 2) of the waveform shaping circuit 208 to a desired level, as well as to isolate the HV power supply 202 and waveform shaping circuit 208 from the electrodes 108 and 140. Such a filter can be, e.g., an RC snubber circuit including a resistor and capacitor connected in series between the electrodes 108 and 140, which filter can be used to filter out high-frequency transients or ringing that may be caused by leakage inductance of a transformer. Such DC blocking capacitors can be used to prevent low frequency or DC currents from inadvertently flowing through patient tissue.

Still referring to FIG. 2, the HV power supply 202 is configured to selectively provide a high voltage DC signal that is used to charge up the HV capacitor(s) 206 to a desired voltage level. In certain embodiments, the voltage sense circuit 210 can be used to determine when the HV capacitor(s) 206 are charged to the desired voltage level, but that need not be the case. The HV power supply 202 can include, e.g., an AC/DC converter that takes in alternating current (AC) mains and outputs a direct current (DC) signal. The HV power supply 202 can also include step-up or step-down voltage regulator that receives the output of the AC/DC converter and converts the output of the AC/DC converter to a desired voltage level and maintains the voltage level at the desired level. The HV power supply 202 can include additional and/or alternative circuitry, as would be appreciated by one of ordinary skill in the art. The switch Sp is used to selectively connect the HV power supply 202 to the HV capacitor(s) 206. Instead of (or in addition to) using the switch Sp to control whether the HV power supply 202 will charge the HV capacitor(s) 206, the output of the HV power supply 202 can be selectively enabled and disabled by the controller 203 to thereby selectively control whether at any given time the HV capacitor(s) 206 will be charged by the HV power supply 202. Accordingly, where the output of the HV power supply 202 can be selectively enabled and disabled by the controller 203, the switch Sp can optionally be eliminated.

The HV capacitor(s) 206 include one or more HV capacitors that are used to store the energy that is used to generate the tissue treatment signal that is delivered to a patient via the electrodes 108 and 140, or some other electrodes. The HV capacitor(s) 206 are likely implemented using a bank of capacitors connected in series and/or in parallel with one another, depending on the specific implementation.

The bleed resistor(s) 207 are used to selectively discharge all or a portion of the energy stored by the HV capacitor(s) 206, by selectively turning ON (i.e., closing) the switch S_bleed. For example, when the voltage sense circuit 210 is used by the controller 203 to determine that the voltage stored by the HV capacitor(s) 206 is above a desired level, the controller 203 can cause the switch S_bleed to be turned ON (i.e., closed) until the voltage stored by the HV capacitor(s) 206 is reduced to the desired level, at which point the controller 203 can cause the switch S_bleed to be turned OFF (i.e., opened). The switches Sp and S_bleed can each be implemented using a respective insulated-gate bipolar transistor (IGBT), another type of transistor, or a relay, but is not limited thereto. The bleed resistor(s) 207 can be implemented using a bank of resistors connected in series and/or in parallel with one another, depending on the specific implementation. It would also be possible to not include any bleed resistor(s), and to instead, bleed any excess voltage stored by the HV capacitor(s) 206 into patient tissue.

The waveform shaping circuit 208 is shown as including current limiting resistors Ra1, Ra2, Rb1, and Rb2, and switches Sa1, Sa2, Sb1, and Sb2. The switches are controlled by the controller 203, which can be implemented by a processor (e.g., the processor 154 in FIGS. 1A and 1B), a field programmable gate array (FPGA), or the like. In accordance with certain embodiments, each of the switches Sa1, Sa2, Sb1, and Sb2 is implemented using a respective insulated-gate bipolar transistor (IGBT). Where each of the switches is implemented using a respective IGBT, each of the switches can include or be associated with a respective IGBT driver (not shown), as would be appreciated by one of ordinary skill in the art. Each such IGBT driver can selectively turn ON (i.e., close) or turn OFF (i.e., open) a respective IGBT type switch responsive to a signal received from the controller 203. Output nodes of the waveform shaping circuit 208, which nodes are labeled Output 1 and Output 2, are respectively connected to the active and return electrodes 108 and 140. Alternatively, if the circuit 158 included a step-up transformer, the Output nodes of the waveform shaping circuit 208, labeled Output 1 and Output 2, can be connected to a primary side of the transformer, and the active and return electrodes 108 and 140 can be connected to a secondary side of the transformer. The aforementioned switches can alternatively be implemented using other types of transistors.

Figures 3, 4:
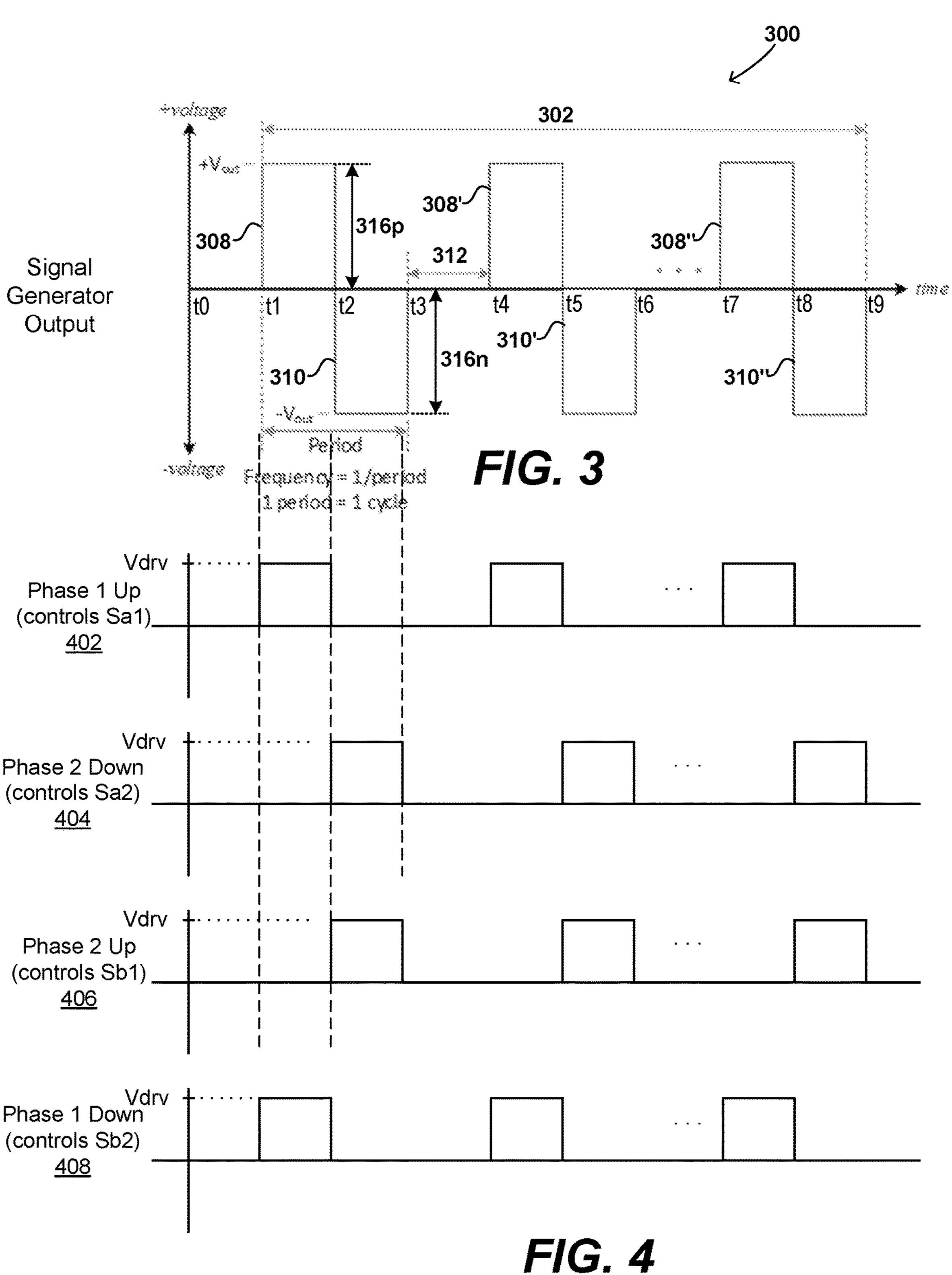
FIG. 3 illustrates an embodiment of a waveform of a biphasic treatment signal prescribed by an energy delivery algorithm.
FIG. 4 illustrates signals generated by a controller of the circuit introduced in FIG. 2 and used to control switches to generate a biphasic treatment signal.

FIG. 3 illustrates an embodiment of a waveform 300 of a treatment signal prescribed by an energy delivery algorithm 152, wherein the waveform 300 can be generated by selectively turning ON and OFF the various switches Sa1, Sa2, Sb1, and Sb2 under the control of the controller 203. The waveform 300 can also be referred to as a biphasic treatment signal 300, or more succinctly as a treatment signal 300. In FIG. 3, one packet 302 is shown. However, the waveform 300 can also include one or more additional packets (not shown), wherein pairs of packets are separated by one another by a rest period. In this embodiment, the packet 302 is comprised of a first biphasic cycle (comprising a first positive pulse peak 308 and a first negative pulse peak 310), a second biphasic cycle (comprising a second positive pulse peak 308' and a second negative pulse peak 310'), and an nth biphasic cycle (comprising an nth positive pulse peak 308" and an nth negative pulse peak 310"), where n is an integer that is greater than or equal to 3. The first and second biphasic pulses are separated by dead time 312 (i.e., a pause) between each pulse. In this embodiment, the biphasic pulses are symmetric so that the set voltage 316*p* for the positive peaks is the same as the set voltage 316*n* for the negative peaks, however that need not be the case. Here, the biphasic, symmetric waves are also square waves such that the magnitude and time of the positive voltage wave is approximately equal to the magnitude and time of the negative voltage wave, however that need not be the case.

When using a bipolar configuration to apply a treatment signal, portions of cells (e.g., airway wall cells) facing the negative voltage wave undergo cellular depolarization in these regions, where a normally negatively charged cell membrane region briefly turns positive. Conversely, portions of the cells facing the positive voltage wave undergo hyperpolarization in which the cell membrane region's electric potential becomes extremely negative. When used to treat airway walls of a patient's lungs, it may be appreciated that in each positive or negative phase of the biphasic pulse, portions of the airway wall cells will experience the opposite effects. For example, portions of cell membranes facing the negative voltage will experience depolarization, while the portions 180 degrees to this portion will experience hyperpolarization. In some embodiments, the hyperpolarized portion faces the dispersive or return electrode 140.

The HV tissue treatment signals described herein can be used, for example, to deliver therapeutic energy to portions a patient's heart to provide tissue modification, such as to the entrances to the pulmonary veins in the treatment of atrial fibrillation (AF). Targeted specific anatomic locations include the superior vena cava, inferior vena cava, right pulmonary vein, left pulmonary vein, right atrium, right atrial appendage, left atrium, left atrial appendage, right ventricle, left ventricle, right ventricular outflow tract, left ventricular outflow tract, ventricular septum, left ventricular summit, regions of myocardial scar, myocardial infarction border zones, myocardial infarction channels, ventricular endocardium, ventricular epicardium, papillary muscles and the purkinje system, to name a few. Treatments are delivered at isolated sites or in a connected series of treatments. Types of treatment include the creation of left atrial roof line, left atrial posterior/inferior line, posterior wall isolation, lateral mitral isthmus line, septal mitral isthmus line, left atrial appendage, right sided cavotricuspid isthmus (CTI), pulmonary vein isolation, superior vena cava isolation, vein of Marshall, lesion creation using Complex Fractionated Atrial Electrograms (CFAE), lesion creation using Focal Impulse and Rotor Modulation (FIRM), and targeted ganglia ablation. Such tissue modification creates a conduction block within the tissue to prevent the transmission of aberrant electrical signals. The devices, systems and methods are typically used in an electrophysiology lab or controlled surgical suite equipped with fluoroscopy and advanced ECG recording and monitoring capability. An electrophysiologist (EP) is the intended primary user of the system. The electrophysiologist will be supported by a staff of trained nurses, technicians, and potentially other electrophysiologists. Generally, the tissue modification systems include a specialized catheter, a high voltage waveform generator and at least one distinct energy delivery algorithm.

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 316 is between about 500 V to 10,000 V, particularly about 500 V to 5000 V, about 500 V to 4000 V, about 1000 V to 4000 V, about 2500 V to 4000V, about 2000 to 3500, about 2000 V to 2500V, about 2500 V to 3500 V, including all values and subranges in between including about 500 V, 1000 V, 1500 V, 2000 V, 2500 V, 3000 V, 3500 V, 4000 V. In some embodiments, each high voltage pulse is in range of approximately 1000 V to 2500 V which can penetrate the airway wall W in particular parameter combinations so as to treat or affect particular cells somewhat shallowly, such as epithelial cells. In some embodiments, each high voltage pulse is in the range of approximately 2500 V to 4000 V which can penetrate the airway W in particular parameter combinations so as to treat or affect particular cells somewhat deeply positioned, such as submucosal cells or smooth muscle cells.

It may be appreciated that the set voltages **316*p*, 316*n*** may vary depending on the specific implementation. In bipolar delivery, a lower voltage may be used due to the smaller, more directed electric field. In some embodiments, the energy is delivered in a bipolar fashion and each pulse is in the range of approximately 100 V to 1900 V, particularly 100 V to 999 V, more particularly approximately 500 V to 800 V, such as 500 V, 550 V, 600 V, 650 V, 700 V, 750 V, 800 V. In other embodiments, the energy is delivered in a bipolar fashion and each pulse is between approximately 50 and 5000 volts, including 250 to 1500 volts.

The voltage selected for use in bipolar therapy is dependent on the separation distance of the electrodes, whereas with monopolar electrode configurations that use a distant dispersive pad electrode may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1-3 mm), if the separation distance is changed from 1 mm to 1.2 mm, this would result in a necessary increase in treatment voltage from 300 to about 360 V, a change of 20%.

The number of biphasic cycles per second of time is the frequency. In some embodiments, biphasic pulses are utilized to reduce undesired muscle stimulation, particularly cardiac muscle stimulation. In other embodiments, the pulse waveform is monophasic, and there is no clear inherent frequency, and instead a fundamental frequency may be considered by doubling the monophasic pulse length to derive the frequency. In some embodiments, the signal has a frequency in the range 10 kHz-10 MHz, more particularly 100 kHz-1 MHz, or more particularly 100 kHz-1000 kHz. In some embodiments, the signal has a frequency in the range of approximately 100-600 kHz which typically penetrates the airway so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates the airway wall W so as to treat or affect particular cells somewhat shallowly, such as epithelial cells. It may be appreciated that at some voltages, frequencies at or below 300 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

FIG. 4 illustrates signals generated by the controller 203 in FIG. 2 (e.g., the processor 154 in FIGS. 1A and 1B) to control the switches Sa1, Sa2, Sb1, and Sb2 to generate the biphasic treatment signal 300 shown in FIG. 3. The aforementioned switches collectively provide for a switching network. In FIG. 4, the phase 1 up signal 402 is used to control the switch Sa1, the phase 2 down signal is used to control the switch Sa2, the phase 2 up signal 406 is used to control the switch Sb1, and the phase 1 down signal 408 is used to control the switch Sb2. Referring to FIGS. 2, 3, and 4, during the period of time between times t1 and t2, the phase 1 up signal 402 turns ON (i.e. closes) the switch Sa1 and the phase 1 down signal 408 turns ON (i.e., closes) the switch Sb2, and the phase 2 down signal 404 keeps the switch Sa2 turned OFF (i.e., open) and the phase 2 up signal 406 keeps the switch Sb1 turned OFF (i.e., open), which results in the first positive pulse peak 308 shown in FIG. 3.

During the period of time between times t2 and t3, the phase 1 up signal 402 turns OFF (i.e. opens) the switch Sa1 and the phase 1 down signal 408 turns OFF (i.e., opens) the switch Sb2, and the phase 2 down signal 404 turns ON (i.e., closes) the switch Sa2 and the phase 2 up signal 406 turns ON (i.e., closes) the switch Sb1, which results in the first negative pulse peak 310 shown in FIG. 3. During the period of time between times t3 and t4, the phase 1 up signal 402 keeps the switch Sa1 turned OFF (i.e., open) and the phase 1 down signal 408 keeps the switch Sb2 turned OFF (i.e., open), and the phase 2 down signal 404 turns OFF (i.e., opens) the switch Sa2 and the phase 2 up signal 406 turns OFF (i.e., opens) the switch Sb1, which results in the dead time 312 that follows first negative pulse peak 310 shown in FIG. 3. During the period of time between times t4 and t5, the phase 1 up signal 402 turns ON (i.e. closes) the switch Sa1 and the phase 1 down signal 408 turns ON (i.e., closes) the switch Sb2, and the phase 2 down signal 404 keeps the switch Sa2 turned OFF (i.e., open) and the phase 2 up signal 406 keeps the switch Sb1 turned OFF (i.e., open), which results in the second positive pulse peak 308' shown in FIG. 3. During the period of time between times t5 and t6, the phase 1 up signal 402 turns OFF (i.e. opens) the switch Sa1 and the phase 1 down signal 408 turns OFF (i.e., opens) the switch Sb2, and the phase 2 down signal 404 turns ON (i.e., closes) the switch Sa2 and the phase 2 up signal 406 turns ON (i.e., opens) the switch Sb1, which results in the second negative pulse peak 310' shown in FIG. 3. During the period of time between times t6 and t7, the phase 1 up signal 402 keeps the switch Sa1 turned OFF (i.e., open) and the phase 1 down signal 408 keeps the switch Sb2 turned OFF (i.e., open), and the phase 2 down signal 404 turns OFF (i.e., opens) the switch Sa2, and the phase 2 up signal 406 turns OFF (i.e., opens) the switch Sb1, which results in a further dead time that follows second negative pulse peak 310' shown in FIG. 3. Additional positive pulse peaks and negative pulse peaks (e.g., 308" and 310") and additional deadtimes can be produced in a similar manner, as desired.

Referring back to FIGS. 1A and 1B, the generator 104 can measure tissue parameters, such as tissue impedance, in order to select appropriate treatment parameters, such as current levels and/or voltage levels. Further, in accordance with certain embodiments of the present technology, the generator 104 can use target current control, and/or target voltage control, to control levels of tissue treatment.

With target current control, which can also be referred to as current set point control, a voltage is adjusted in order to treat tissue with a target current. More specifically, with target current control, a tissue impedance is measured, and a voltage is selected to achieve a target current. For an example, if a target current is 30 amps (A), and a measured tissue impedance is 100 ohms (Ω), then the voltage can be adjusted to be 3000 volts (V), since V=I*R=30 A*100 Ω=3000 V. For another example, if the target current is 30 amps (A), and a measured tissue impedance is 80 ohms (Ω), then the voltage can be adjusted to be 2400 volts (V), since V=I*R=30 A*80 Ω=2400 V. For still another example, if the target current is 30 amps (A), and a measured tissue impedance is 120 ohms (Ω), then the voltage can be adjusted to be 3600 volts (V), since V=I*R=30 A*120 Ω=3600 V. The HV voltage sense circuit 210 can be used to determine when the voltage stored on the HV capacitor(s) 206 is at the desired level. Alternatively, or additionally, the HV voltage sense circuit 212 can be used to determine whether the target voltage is being delivered to patient tissue, and can be used as feedback to increase or decrease to what voltage level the HV capacitor(s) 206 should be charged. The HV current sense circuit 214 can be used to measure the current delivered to patient tissue via the active electrode 108, which measurement can be used as feedback to increase or decrease to what voltage level the HV capacitor(s) 206 should be charged. An advantage of using target current control, which can also be referred to as current set point control, it that target current control enables a tissue treatment system to compensate for electrode array and tissue impedance variations in delivering PEF treatments. This allows the production of more consistent treatment effects, leading to more predictable results. This allows for improved efficacy, especially in patient's having high tissue impedance, and also provides for improved safety, by reducing the chance of overtreatment, injury, and arcing in patient's having low tissue impedance.

With target voltage control, which can also be referred to as voltage set point control, a current is adjusted in order to treat tissue with a target voltage. More specifically, with target voltage control, a tissue impedance is measured, and a current is selected to achieve the target voltage. For an example, if a target voltage is 3000 V, and a measured tissue impedance is 100Ω, then the current can be adjusted to be 30 A, since I=V/R=3000 V/100 Ω=30 A. For another example, if the target voltage is 3000 V, and a measured tissue impedance is 80 ohms (Ω), then the current can be adjusted to be 37.5 A, since I=V/R=3000 V/80 Ω=37.5 A. For still another example, if the target voltage is 3000 V, and a measured tissue impedance is 120Ω, then the current can be adjusted to be 25 A, since I=V/R=3000 V/120 Ω=25 A.

As can be appreciated from the above discussion, whether the generator 104 is performing target current control or target voltage control, tissue impedance should be measured so that an appropriate adjustment can be made to the tissue treatment voltage level or current level, if needed, in order to provide a target current or a target voltage. In accordance with certain embodiments, tissue impedance is measured (for a specific location within a specific body lumen, such as a pulmonary vein) by advancing the active electrode 108 of the instrument 102 to the desired location, delivering a relatively low voltage pulse (e.g., 100 V), measuring a current using a current sense circuit (e.g., 214 in FIG. 2), and calculating the impedance using the equation R=V/I. For an example, if the measured current was 0.8 A, then the tissue impedance can be calculated as R=100 V/0.8 A=125Ω. For another example, if the measured current was 1.0 A, then the tissue impedance can be calculated as R=100 V/1.0 A=100Ω. The reason a relatively low voltage pulse (e.g., 100 V) is used to determine tissue impedance is that the voltage pulse should be below the level at which a treatment effect occurs. In accordance with certain embodiments of the present technology, the voltage of the low voltage pulse that is used to determine tissue impedance is within the range of 1 V to 100 V, but are not limited thereto. The low voltage (LV) pulses, or more generally LV signals, that are generated and used to determine tissue impedance can be referred to herein as LV impedance measurement signals. By contrast, the high voltage (HV) pulses, or more generally HV signals, that are generated and used to effect treatment can be referred to herein as HV tissue treatment signals, or more succinctly as HV treatment signals.

The LV tissue impedance measurement signals discussed herein include one or more voltages pulses that each have a peak-to-peak voltage that does not exceed 100 V, and more specifically, a peak-to-peak voltage within the range of 1 V to 100 V. The HV tissue treatment signals discussed herein include one or more voltages pulses that each have a peak-to-peak voltage of at least 500 V, and more specifically, a peak-to-peak voltage within the range of 500 V to 10,000 V. In specific embodiments, the peak-to-peak voltage of each of the pulses of the HV tissue treatment signal is at least five times greater than the peak-to-peak voltage of each of the pulses of the LV tissue impedance measurement signal, e.g., if the LV voltage pulses are 50 V, the HV voltage pulses are at least 500 V.

Referring back to FIG. 2, if the output signal generator 158 were to be used to generate HV treatment signals (e.g., within the range of 2500 V to 3500 V), as well as to generate LV impedance measurement signals (e.g., within the range of 10 V to 100 V) that are used to determine tissue impedance, then the voltage stored on the HV capacitor(s) 206 would need to be significantly reduced each time there was a transition from using the output signal generator 158 to generate a HV treatment signal to using the output signal generator 158 to generate a LV impedance measurement signal. Additionally, the voltage stored on the HV capacitor(s) 206 would need to be significantly increased each time there was a transition from using the output signal generator 158 to generate a LV impedance measurement signal to using the output signal generator 158 to generate a HV treatment signal. Such increasing and decreasing of the voltage stored on the HV capacitor(s) 206 can be time consuming, which can increase the overall time it takes for a physician to perform a treatment procedure.

In accordance with certain embodiments of the present technology, rather than relying upon the same circuitry to produce both HV treatment signals and LV impedance measurement signals, separate circuitry is used to generate the LV impedance measurement signals than is used to generate the HV treatment signals. In such embodiments, a same controller (e.g., an FPGA or a processor) can be used for controlling the generation of both the HV treatment signals and LV impedance measurement signals. A high level block diagram of such an embodiment is shown in FIG. 5A.

Figure 5A:
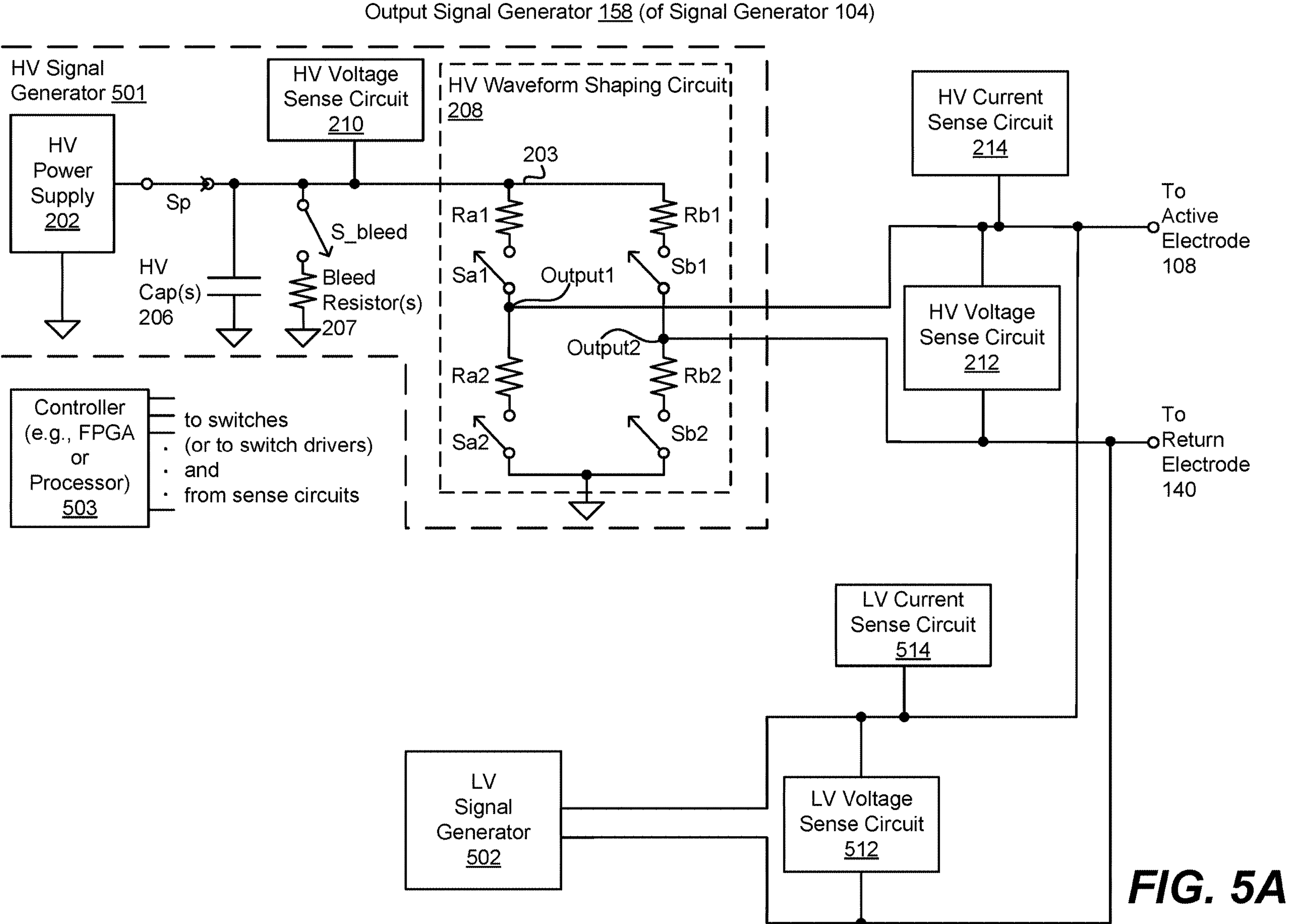
FIG. 5A is a high level block diagram of the output signal generator, of the signal generator introduced in FIGS. 1A and 1B, according to an embodiment of the present technology.

Referring to FIG. 5A, shown therein is a HV signal generator 501, a LV signal generator 502, and a controller 503 that is used to control generation of the HV treatment signals and LV impedance measurement signals by the HV signal generator 501 and the LV signal generator 502, respectively. In FIG. 5A, the HV signal generator 501 is shown as including the HV power supply 202, the HV capacitor(s) 206, and the waveform shaping circuit 208, that were described above with reference to FIG. 2, and thus, need not be described again. In other embodiments, the HV signal generator 502 can include alternative and/or additional circuitry.

Still referring to FIG. 5A, the HV voltage sense circuit 212 is used to sense the voltage between the active electrode 108 and the return electrode 140 when the HV signal generator 501 is being used and/or is about to be used to generate a HV treatment signal. The HV current sense circuit 214 is used to sense the current delivered via the active electrode 108 when the HV signal generator 501 is being used and/or is about to be used to generate a HV treatment signal. Also shown in FIG. 5A is a LV voltage sense circuit 512 that is used to sense the voltage between the active electrode 108 and the return electrode 140 when the LV signal generator 503 is being used and/or is about to be used to generate a LV impedance measurement signal. The LV current sense circuit 514 is used to sense the current delivered via the active electrode 108 when the LV signal generator 502 is being used and/or is about to be used to generate a LV impedance measurement signal.

A benefit of using the HV voltage sense circuit 212 when a HV treatment signal is being generated, and using the LV voltage sense circuit 512 when a LV impedance measurement signal is being generated, is that the resolution of the measurements produced by the sense circuit 212 and the resolution of the measurements produced by the sense circuit 512 can be specifically tailored to and optimized, respectively, for the range of expected HV measurements the range of expected LV measurements. By contrast, if a same voltage sense circuit were instead used to sense the voltage between the active electrode 108 and the return electrode 140 when the HV signal generator 501 was being used, as well as to sense the voltage between the active electrode 108 and the return electrode 140 when the LV signal generator 502 was being used, then the resolution of the HV measurements and/or the LV measurements would be compromised (i.e., less optimal).

A benefit of using the HV current sense circuit 214 when a HV treatment signal is being generated, and using the LV current sense circuit 514 when a LV impedance measurement signal is being generated, is that the resolution of the measurements produced by the sense circuit 214 and the resolution of the measurements produced by the sense circuit 514 can be specifically tailored to and optimized, respectively, for the range of expected HV current measurements the range of expected LV current measurements. By contrast, if a same current sense circuit were instead used to sense the current provided to the active electrode 108 when the HV signal generator 501 was being used, as well as to sense the current provided to the active electrode 108 when the LV signal generator 502 was being used, then the resolution of the HV current measurements and/or the LV current measurements would be compromised (i.e., less optimal).

FIG. 5B shows example details of how the LV signal generator 502 can be implemented in a similar manner as the HV signal generator 501. Referring to FIG. 5B, in this example, the LV signal generator 502 is shown as including a LV power supply 504, LV capacitor(s) 206, and a waveform shaping circuit 508. The LV power supply 504 is configured to selectively provide a low voltage DC signal that is used to charge up the LV capacitor(s) 206 to a desired voltage level. In certain embodiments, a voltage sense circuit 510 can be used to determine when the LV capacitor (s) 506 are charged to the desired voltage level, but that need not be the case. The LV power supply 504 can include, e.g., an AC/DC converter that takes in AC mains and outputs a DC signal. The LV power supply 504 can also include step-up or step-down voltage regulator that receives the output of the AC/DC converter and converts the output of the AC/DC converter to a desired voltage level and mains the voltage level at the desired level. The LV power supply 504 can include additional and/or alternative circuitry, as would be appreciated by one of ordinary skill in the art. The switch Sp2 is used to selectively connect the LV power supply 504 to the LV capacitor(s) 506. Instead of (or in addition to) using the switch Sp2 to control whether the LV power supply 504 will charge the LV capacitor(s) 506, the output of the LV power supply 504 can be selectively enabled and disabled by a controller 503 to thereby selectively control whether at any given time the LV capacitor(s) 506 will be charged by the LV power supply 504. Accordingly, where the output of the LV power supply 504 can be selectively enabled and disabled by the controller 503, the switch Sp2 can optionally be eliminated. In FIG. 5B, the LV waveform shaping circuit 508, which is similar to wave shaping circuit 208 described above, can be used to generate a pulsed or square wave LV impedance measurement signal.

Still referring to FIG. 5B, in an alternative embodiment, the LV capacitor(s) 506 can be completely eliminated, if the LV power supply 504 outputs a voltage of a sufficient magnitude that energy does not need to be stored on any capacitor(s) to produce the LV impedance measurement signals. It is also noted that the waveform shaping circuit 508 can be different than show, e.g., if the LV impedance measurement signals have a sinusoidal or other shaped waveform. Accordingly, embodiments of the present technology are not limited to the specific waveform shaping circuits 508 and 208 shown and described herein. For example, where the LV impedance measurement signals are sinusoidal, an LV waveform shaping circuit can be implemented using an oscillator, such as a Wien bridge oscillator, or a Colpitts type crystal oscillator, but not limited thereto.

The bleed resistor(s) 507 are used to selectively discharge all or a portion of the energy stored by the LV capacitor(s) 506, by selectively turning ON (i.e., closing) the switch S_bleed2. For example, when the LV voltage sense circuit 510 is used by the controller 503 to determine that the voltage stored by the LV capacitor(s) 506 is above a desired level, the controller 503 can cause the switch S_bleed2 to be turned ON (i.e., closed) until the voltage stored by the LV capacitor(s) 506 is reduced to the desired level, at which point the controller 503 can cause the switch S_bleed2 to be turned OFF (i.e., opened). The switches Sp2 and S_bleed2 can each be implemented using a respective insulated-gate bipolar transistor (IGBT), another type of transistor, or a relay, but is not limited thereto. The bleed resistor(s) 507 can be implemented using a bank of resistors connected in series and/or in parallel with one another, depending on the specific implementation. It would also be possible to not include any bleed resistor(s), and to instead, bleed any excess voltage stored by the LV capacitor(s) 506 into patient tissue.

Figure 5C:
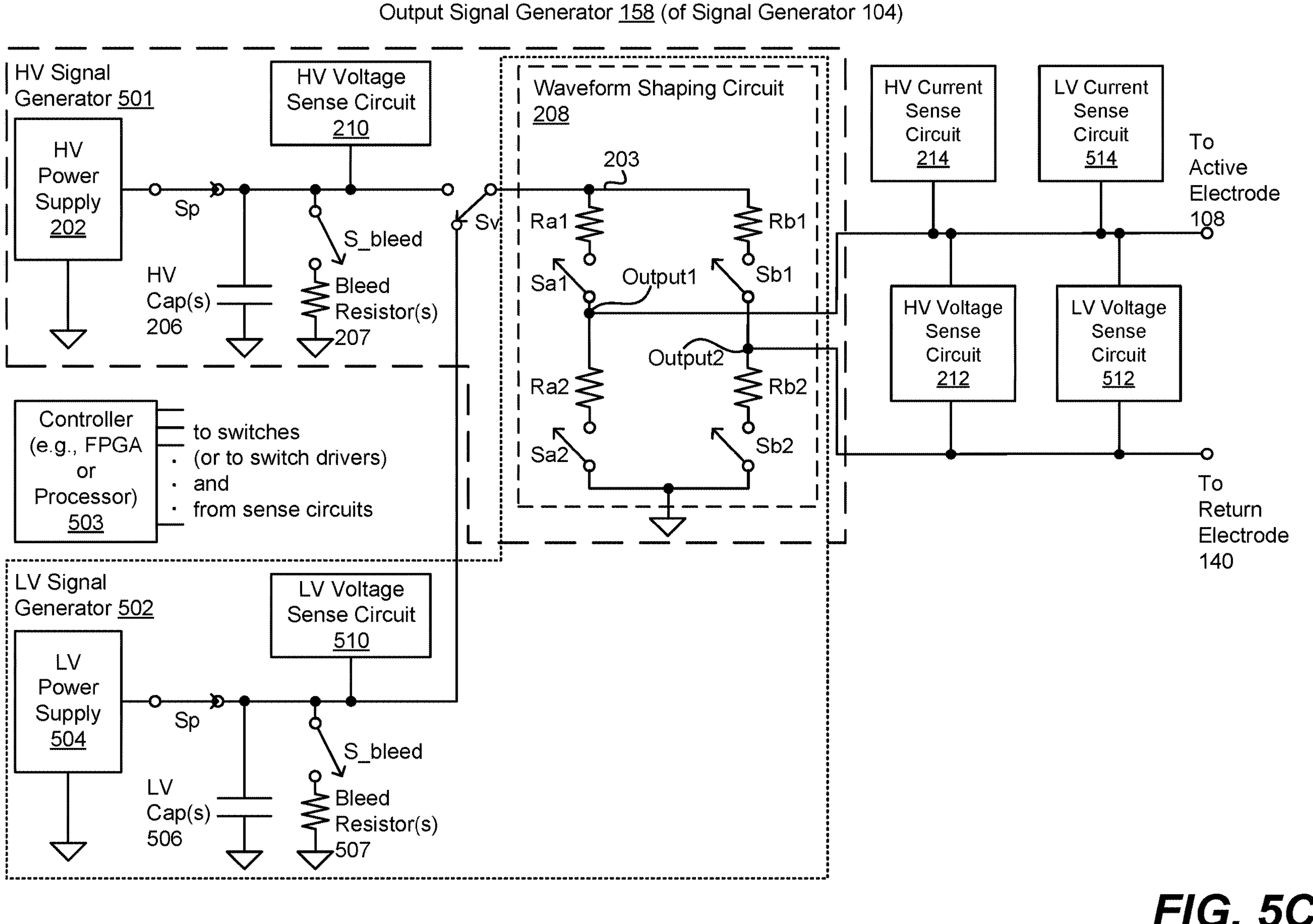
FIG. 5C is a high level block diagram of the output signal generator, according to a further embodiment of the present technology.

FIG. 5C shows example details of how the LV signal generator 502 can be implemented in accordance with another embodiment, wherein the same waveform shaping circuit 208 is shared by both the HV signal generator 501 and the LV signal generator 502. In the embodiment of FIG. 5C, there is a switch Sv that is controlled, by the controller 503, to either couple the HV power supply 202 (and/or the HV capacitor(s) 206) to the waveform shaping circuit 208, or to couple the LV power supply 504 (and/or the LV capacitor(s) 506) to the waveform shaping circuit 208. While the switch Sv couples the HV power supply 202 (and/or the HV capacitor(s) 206) to the waveform shaping circuit 208, the waveform shaping circuit 208 is part of the HV signal generator 501. While the switch Sv couples the LV power supply 504 (and/or the LV capacitor(s) 506) to the waveform shaping circuit 208, the waveform shaping circuit 208 is part of the LV signal generator 502. Still referring to FIG. 5C, in an embodiment the LV capacitor(s) 506 can be completely eliminated, if the LV power supply 504 outputs a voltage of a sufficient magnitude that energy does not need to be stored on any capacitor(s) to produce the LV impedance measurement signals. It is also noted that the waveform shaping circuit 208, which is shared by both generators 501, 502, can be different than show, while still being within the scope of the embodiments described herein.

Figure 5D:
FIG. 5D is a high level block diagram of the output signal generator, according to still another embodiment of the present technology.

FIG. 5D shows example details of how the LV signal generator 502 can be implemented in accordance with still another embodiment. In the embodiment of shown in FIG. 5D, when the Sp switch is closed and/or the HV power supply 202 is enabled, and the Sv1 switch is closed and the Sv2 switch is open, the HV power supply will charge up one or more HV capacitors 206, as well as charge up one or more LV capacitors 506. Since the capacitance of the LV capacitor(s) 506 is significantly less than the capacitance of the HV capacitor(s) 206 (e.g., no more than one fifth the capacitance of the HV capacitor(s) 206), the magnitude of the voltage stored on the LV capacitor(s) 506 will be significantly less than the magnitude of voltage collectively stored on the HV capacitor(s) 206 and the LV capacitor(s) 506 (e.g., no more than one fifth voltage collectively stored in the HV capacitor(s) and the LV capacitor(s) 506). In the embodiment of FIG. 5D, when the switch Sv1 is closed, and the switch Sv2 is open, the charge collectively stored on the HV capacitor(s) 206 and the LV capacitor(s) 506 is provided to the waveform shaping circuit 208 and used to produce a HV treatment signal. When the switch Sv is open, and the switch Sv2 is closed, only the charge stored on the LV capacitor(s) 506 is provided to the waveform shaping circuit 208 and used to produce a LV impedance measurement signal. In this manner, the HV power supply 202 is shared by both the HV signal generator 501 and the LV signal generator 502. Other variations are also possible and within the scope of the embodiments described herein. For example, a single pole double throw switch can be used in place of the two single pole single throw switches Sv1 and Sv2, such that when the single pole double throw switch is in a first position the voltage collectively stored on the HV capacitor(s) 206 and the LV capacitor(s) 506 is provided to the waveform shaping circuit 208 and used to produce a HV treatment signal, and such that when the single pole double throw switch is in a second position only the voltage stored on the LV capacitor(s) is provided to the waveform shaping circuit 208 and used to produce a LV impedance measurement signal.

More generally, in the embodiment of FIG. 5D, the controller 503 can control various switches to cause a first subset of the capacitors 206, 506 to be coupled to the waveform shaping circuit 208 during a first period of time during which a LV tissue impedance measurement signal is to be delivered to patient tissue via the electrodes 108, 140, and to cause a second subset of the capacitors 206, 506 to be coupled to the waveform shaping circuit 208 during a second period of time during which a HV tissue treatment signal is to be delivered to the patient tissue via the electrodes 108, 140. In such embodiments, a voltage of the HV tissue treatment signal is at least five times greater than a voltage of the LV tissue impedance measurement signal. Additionally, in such embodiments, the first subset of the capacitors includes at least one of the plurality of capacitors 206, 506, and the second subset of the capacitors includes at least one of the plurality of capacitors and differs from the first subset. In FIG. 5D, the bleed resistor(s) 207 can be used to selectively discharge all or a portion of the energy stored by the capacitors 206 and 506, by selectively turning ON (i.e., closing) the switch S_bleed. It would also be possible to not include any bleed resistor(s), and to instead, bleed any excess voltage stored by the capacitors 206 and 506 into patient tissue.

In FIGS. 5A, 5B, 5C, and 5D, the HV voltage sense circuit 212 is used to sense the voltage between the active electrode 108 and the return electrode 140 when the HV signal generator 501 is being used and/or is about to be used to generate a HV treatment signal, and the LV voltage sense circuit 512 that is used to sense the voltage between the active electrode 108 and the return electrode 140 when the LV signal generator 503 is being used and/or is about to be used to generate a HV treatment signal. A benefit of using the HV voltage sense circuit 212 when a HV treatment signal is being generated, and using the LV voltage sense circuit 512 when a LV impedance measurement signal is being generated, is that the resolution of the measurements produced by the sense circuit 212 and the resolution of the measurements produced by the sense circuit 512 can be specifically tailored to and optimized, respectively, for the range of expected HV measurements the range of expected LV measurements. In an alternative embodiment, a same voltage sense circuit can be used regardless of whether a HV treatment signal or a LV impedance measurement signal is being produced. However, in such an alternative embodiment the resolution of the HV voltage measurements and/or the LV voltage measurements will be compromised (i.e., less optimal).

In FIGS. 5A, 5B, 5C, and 5D, the HV current sense circuit 214 is used when a HV treatment signal is being generated, and the LV current sense circuit 514 is used when a LV impedance measurement signal is being generated. A benefit of using the HV current sense circuit 214 when a HV treatment signal is being generated, and using the LV current sense circuit 514 when a LV impedance measurement signal is being generated, is that the resolution of the measurements produced by the sense circuit 214 and the resolution of the measurements produced by the sense circuit 514 can be specifically tailored to and optimized, respectively, for the range of expected HV current measurements the range of expected LV current measurements. In an alternative embodiment, a same current sense circuit is used to sense the current provided to the active electrode 108 when the HV signal generator 501 is being used, as well as to sense the current provided to the active electrode 108 when the LV signal generator 502 is being used. However, in such an alternative embodiment the resolution of the HV current measurements and/or the LV current measurements will be compromised (i.e., less optimal).

In FIGS. 5A, 5B, 5C, and 5D, the output signal generator circuit 158 can include additional circuitry, which is not shown, as would be appreciated by one of ordinary skill in the art. For example, a step-up transformer, a filter, and/or DC blocking capacitors can optionally be coupled between the output nodes (labeled Output 1 and Output 2) of the waveform shaping circuit 208 and the active and return electrodes 108, 140. Such a step-up transformer can be used to step up the voltage signal generated between the output nodes (Output 1 and Output 2) of the waveform shaping circuit 208 to a desired level, as well as to isolate the HV power supply 202 and waveform shaping circuit 208 from the electrodes 108 and 140. Such a filter can be, e.g., an RC snubber circuit including a resistor and capacitor connected in series between the electrodes 108 and 140, which filter can be used to filter out high-frequency transients or ringing that may be caused by leakage inductance of a transformer. Such DC blocking capacitors can be used to prevent low frequency or DC currents from inadvertently flowing through patient tissue.

In certain embodiments, the LV current sense circuit 514 measures the current delivered to patient tissue via the active electrode 108 while the LV tissue impedance measurement signal (produced using the LV signal generator 502) is delivered to the patient tissue, and the HV current sense circuit 214 measures the current delivered to the patient tissue via the active electrode 108 while the HV tissue treatment measurement signal (produced using the HV signal generator 501) is delivered to the patient tissue. In such embodiments, the controller 503 can produce an estimate of an impedance of the patient tissue based on the voltage of the LV tissue impedance measurement signal that is delivered to the patient tissue and based on the current measured by the LV current sense circuit 514. Additionally, the controller 503 can set a voltage of the HV tissue treatment signal (produced using the HV signal generator 501), based on the estimate of the impedance of the patient tissue, and the controller 503 can adjust the voltage of the HV tissue treatment signal (produced using the HV signal generator 501) based on the current measured by the HV current sense circuit 214.

The terms high voltage (HV) and low voltage (LV), as used herein, are terms that are relative to one another, wherein a voltage that is considered to be HV is at least five times greater than a voltage that is considered to be LV. In specific embodiments, a LV signal has a voltage of no more than 100V, and a HV signal has a voltage that is at least five times greater than the LV signal. In certain embodiments, a HV signal has a magnitude of at least 1000V. More generally, the LV signals described herein are used to measure the impedance of patient tissue, as opposed to being used to treat (e.g., ablate) tissue, and thus, a LV signal is often referred to herein as a LV tissue impedance measurement signal. By contrast, the HV signals described herein are used to treat (e.g., ablate) tissue, and thus, a HV signal is often referred to herein as a HV tissue treatment signal, or more succinctly as a HV treatment signal.

In each of the embodiments described above with reference to FIGS. 5A-5D, the output signal generator 158 of the signal generator 104, introduced in FIGS. 1A and 1B, are shown as including both a HV signal generator 501 and a LV signal generator 502, as well as a controller 503. In such embodiments, the LV signal generator 502 is used to produce a LV tissue impedance measurement signal, and the HV signal generator 501 is used to produce a HV tissue treatment signal having a voltage that is at least five times greater than a voltage of the LV tissue impedance measurement signal. The controller 503 controls when the HV tissue treatment signal (produced using the HV signal generator 501), and when the LV tissue impedance measurement signal (produced using the LV signal generator 502), are delivered to patient tissue via an active electrode 108 and a return electrode 140. The controller 503 can control the generation and delivery of such signals by controlling the various switches shown in FIGS. 5A-5D, and/or controlling when various components (e.g., power supply(ies)) are enabled or disabled, as could be appreciated from the above discussion of FIGS. 5A-5D.

In certain embodiments, the LV current sense circuit 514 measures a current that is delivered to the patient tissue via the active electrode 108, while the LV tissue impedance measurement signal, which is produced using the LV signal generator 502, is delivered to the patient tissue. In certain such embodiments, the controller 503 produces an estimate of an impedance of the patient tissue based on the voltage of the LV tissue impedance measurement signal (produced using the LV power supply 504) that is delivered to the patient tissue and based on the current measured by the LV current sense circuit 514, and the controller 503 controls the voltage of the HV tissue treatment signal (produced using the HV signal generator 501) based on the estimate of the impedance of the patient tissue.

In certain embodiments, the controller 503 controls the voltage of the HV tissue treatment signal (produced using the HV signal generator 501), based on the estimate of the impedance of the patient tissue, so that the patient tissue is treated with a current that is approximately equal to a predetermined target current when the HV tissue treatment signal is delivered to the patient tissue. The predetermined target current can be a default target current whose value is stored in memory or a register of the generator 104, or can be specified by a clinician using the user interface 150 of the generator 104.

In certain embodiments, in-between each of a plurality of separate instances of the HV signal generator 501 being used to produce the HV tissue treatment signal that is delivered to the patient tissue, the controller 503 causes the LV signal generator 502 to be used to produce the LV tissue impedance measurement signal that is delivered to the patient tissue. The controller 503 produces an updated estimate of the impedance of the patient tissue based on the voltage of the LV tissue impedance measurement signal that is delivered to the patient tissue and based on an updated measure of the current that is delivered to the patient tissue, as measured using the LV current sense circuit 514. The controller 503 then adjusts the voltage of the HV tissue treatment signal, produced using the HV signal generator 501, if the updated estimate of the impedance of the patient tissue differs from the immediately preceding estimate of the impedance of the patient tissue. In this manner, the patient tissue is treated with a current that is approximately equal to the predetermined target current when the HV tissue treatment signal is next delivered to the patient tissue.

Figure 6:
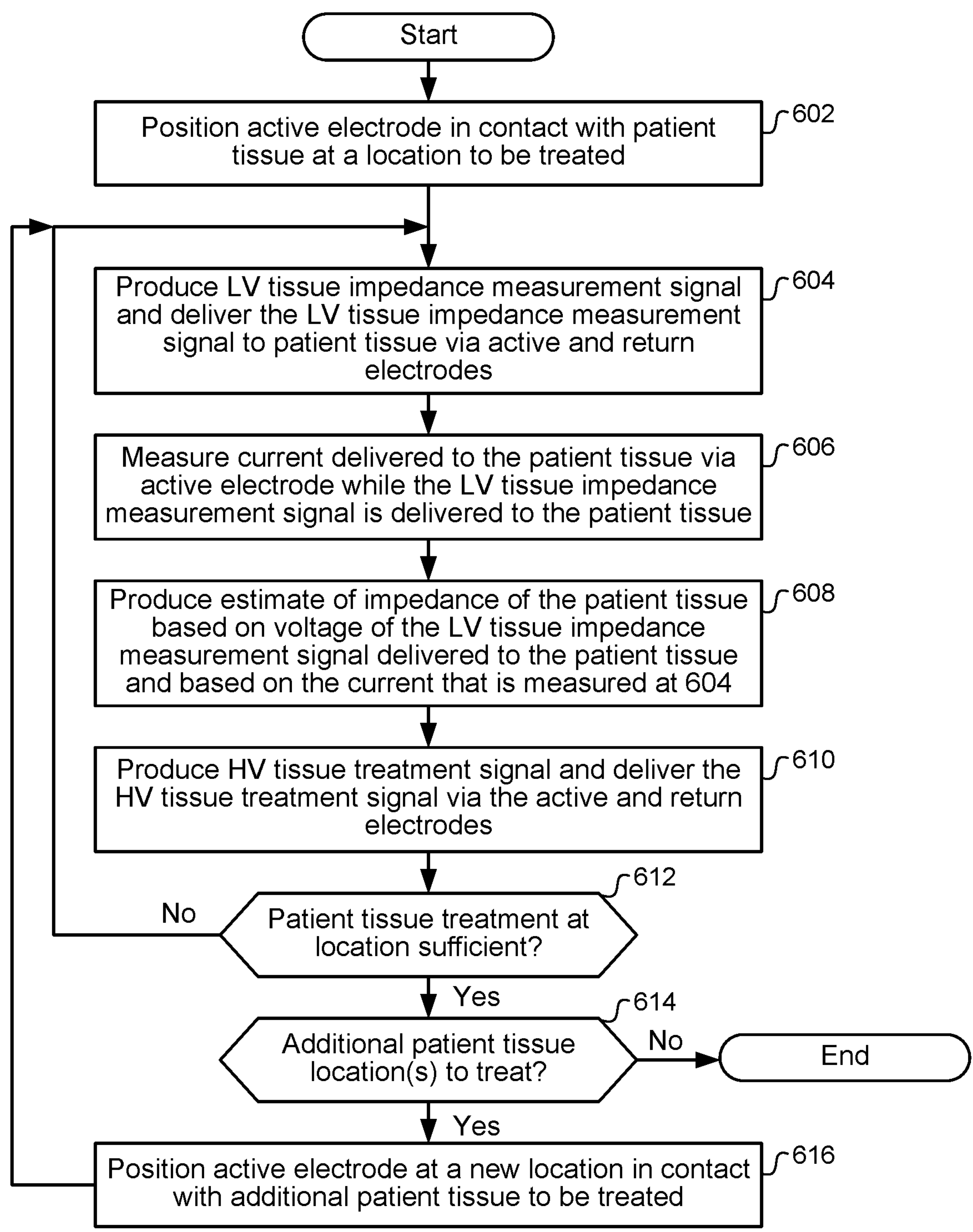
FIG. 6 is a high level flow diagram used to describe methods according to certain embodiments of the present technology.

The high level flow diagram shown in FIG. 6 will now be used to describe methods according to certain embodiments of the present technology, which methods are for use with an output signal generator (e.g., 158) of a signal generator (e.g., 104), where the output signal generator includes both a HV signal generator (e.g., 501) and a LV signal generator (e.g., 502). Referring to FIG. 6, step 602 involves positioning an active electrode of a therapeutic energy delivery instrument, such as a catheter, so that the active electrode is in contact with patient tissue at a location to be treated. An example of such an active electrode is the electrode 108 of the instrument (e.g., catheter) 102 shown in and discussed above with reference to FIG. 1A. Step 602, or a separate step, can also involve applying a return electrode, e.g., 140, externally to the skin of a patient. The return electrode, e.g., 140, can alternatively be an implanted electrode, located, e.g., on the catheter or a sheath, but not limited thereto.

Still referring to FIG. 6, step 604 involves producing a LV tissue impedance measurement signal and delivering the LV tissue impedance measurement signal to patient tissue via the active electrode and the return electrode. The LV tissue impedance measurement signal produced at step 604 can be produced using a signal generator, e.g., 104, or more specifically, an output signal generator 158 thereof. Example implementations of the output signal generator 158 are shown in and described above with reference to FIGS. 5A through 5D. The therapeutic energy delivery instrument, e.g., 102, can be used to deliver the LV tissue impedance measurement signal to patient tissue at step 604, as was described above in great detail.

Step 606 involves measuring a current that is delivered to the patient tissue via the active electrode, e.g., 108, while the LV tissue impedance measurement signal is delivered to the patient tissue. Step 606 can be performed, at least in part, using a current sense circuit, such as, but not limited to, the circuits 514 or 214 discussed above.

Step 608 involves producing an estimate of an impedance of the patient tissue based on a voltage of the LV tissue impedance measurement signal that is delivered to the patient tissue and based on the current that is measured. Step 608 can be performed, at least in part, by a controller, such as the controllers 203 or 503 discussed above. Assume for example that the LV tissue impedance measurement signal delivered at step 604 was a 100 V pulse, and that the current measured at step 606 is 0.8 Amps, then the estimate produced at step 608 can be 125 Ohms, because R=100 V/0.8 A=125Ω. For another example, if the measured current was 1.0 A, then the tissue impedance can be calculated as R=100 V/1.0 A=100Ω.

Step 610 involves producing a HV tissue treatment signal and delivering the HV tissue treatment signal via the active and return electrodes. As was described above, the voltage of the HV tissue treatment signal is at least five times greater than the voltage of the LV tissue impedance measurement signal. As was also described above, producing the HV treatment signal includes controlling the voltage of the HV tissue treatment signal based on the estimate of the impedance of the patient tissue. For example, assuming target current control is being used, which can also be referred to as current set point control, step 610 can include adjusting a voltage in order to treat tissue with a target current. For an example, if a target current is 30 A, and an estimated tissue impedance is 100Ω, then the voltage can be adjusted to be 3000 V, since V=I*R=30 A*100 Ω=3000 V. For another example, if the target current is 30 A, and an estimated tissue impedance is 80Ω, then the voltage can be adjusted to be 2400 V, since V=I*R=30 A*80 Ω=2400 V. For still another example, if the target current is 30 A, and an estimated tissue impedance is 120Ω, then the voltage can be adjusted to be 3600 V, since V=I*R=30 A*120 Ω=3600 V. The HV voltage sense circuit 210 can be used to determine when the voltage stored on the HV capacitor(s) 206 is at the desired level. Alternatively, or additionally, the HV voltage sense circuit 212 can be used to determine whether the target voltage is being delivered to patient tissue, and can be used as feedback to increase or decrease to what voltage level the HV capacitor(s) 206 should be charged. The HV current sense circuit 214 can be used to measure the current delivered to patient tissue via the active electrode 108, which measurement can be used as feedback to increase or decrease to what voltage level the HV capacitor(s) 206 should be charged.

Still referring to FIG. 6, step 612 involves determining whether the patient tissue treatment at the location was sufficient. In certain embodiments, step 612 can be performed by determining whether the impedance of the patient tissue was reduced by at least a specified amount, since the impedance of successfully treated tissue should be significantly reduced. More specifically, steps 604, 606, and 608 can be repeated to produce an updated estimate of the impedance of the patient tissue, and then there can be a determination of whether there was at least a specified reduction (e.g., a reduction of at least 50%) in the impedance of the patient tissue. If there was not at least the specified reduction in the tissue impedance (i.e., if the answer to the determination at step 612 is No), then an additional HV tissue treatment signal is produced and delivered to the same location at another instance of step 610, as could be appreciated from FIG. 6. More specifically, additional instances of steps 604, 606 and 608 can be performed as part of step 612, and then step 610 can be repeated to produce and deliver a further HV tissue treatment signal at the same location (using an updated estimate of tissue impedance produced at the most recent instance of step 608). If there was at least the specified reduction in the tissue impedance (i.e., if the answer to the determination at step 612 is Yes), then flow goes to step 614.

At step 614 there is a determination of whether there is/are any additional patient tissue location(s) to treat. If the answer to the determination at step 614 is No, then the method may end. However, if the answer to the determination at step 614 is Yes, then flow goes to step 616. At step 616 the active electrode, e.g., 108, is positioned at a new location so that it is in contact with additional patient tissue to be treated. Flow then returns to step 604, as shown in FIG. 6. Steps 604, 606, 608, 610 and 612 are then performed while the active electrode is in contact with the additional patient tissue to be treated. This process is then repeated until all the tissue that is to be treated, has indeed been treated, as could be appreciated from FIG. 6.

As explained above in the discussion of FIG. 3, the HV tissue treatment signal produced and delivered at each instance of step 610 can include one or more packets of pulses, wherein the pulses can be biphasic, or alternatively monophasic. Prior to each delivery of a packet of pulses, tissue impedance can be measured, and more specifically estimated, at instances of steps 604, 606 and 608, and based on the measured tissue impedance, a voltage can adjusted as part of an instance of step 610 in order to treat tissue with a target current, or a current is adjusted in order to treat tissue with a target voltage, depending upon whether target current control or target voltage control is being used. Thereafter, updated estimates of tissue impedance can be produced to determine whether an additional HV tissue treatment signal should be delivered to specific patient tissue, or to determine that the specific patient tissue has already been sufficiently treated. In other words, prior to delivery of an initial packet of HV tissue treatment pulses, as well as between successive packets of HV treatment pulses, tissue impedance can be estimated and used to adjust a voltage or a current.

Depending upon the specific implementation, step 612 can be performed following each packet of HV pulses that are generated and delivered at an instance of step 610. Alternatively, step 612 can be performed following a series of packets of HV pulses being generated and delivered at an instance of step 610. Other variations are also possible and within the scope of the embodiments described herein. Either way, near real-time feedback is provided to determine whether additional treatment of a patient tissue location is to be performed, and if so, such near real-time feedback can be used to adjust the current and/or voltage of the HV tissue treatment pulses delivered at a next instance of step 610. Accordingly, the embodiments summarized with reference to FIG. 6 provide for intermittent monitoring of impedance during treatment delivery, in order to determine whether additional treatment at a location should be performed, or whether the active electrode can be moved to a new location.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 5A through 5D, as well as change the order of various steps. For another example, it is possible to change the boundaries of some of the blocks shown in FIGS. 1A through 2C.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A tissue treatment system that is configured to deliver a predetermined target current to patient tissue during a treatment procedure, wherein the predetermined target current comprises a default target current specified prior to beginning the treatment procedure or is specified by a clinician using a user interface of the tissue treatment system prior to beginning the treatment procedure, the tissue treatment system comprising:

- a low voltage (LV) signal generator used to produce a LV tissue impedance measurement signal;
- a high voltage (HV) signal generator used to produce a HV tissue treatment signal having a voltage that is at least five times greater than a voltage of the LV tissue impedance measurement signal;
- a current sense circuit configured to measure a current that is delivered to the patient tissue via an active electrode while the LV tissue impedance measurement signal, which is produced using the LV signal generator, is delivered to the patient tissue; and
- a controller configured to
  - control when the HV tissue treatment signal produced using the HV signal generator, and when the LV tissue impedance measurement signal produced using the LV signal generator, are delivered to patient tissue via the active electrode and a return electrode;
  - produce an estimate of an impedance of the patient tissue based on the voltage of the LV tissue impedance measurement signal that is delivered to the patient tissue and based on the current measured by the current sense circuit; and
  - adjust the voltage of the HV tissue treatment signal produced using the HV signal generator during the treatment procedure, based on the estimate of the impedance of the patient tissue and one or more updates thereto, so that when the HV tissue treatment signal is delivered to the patient tissue during the treatment procedure the patient tissue is treated with a current that is approximately equal to the predetermined target current that was specified prior to beginning the treatment procedure.

2. The tissue treatment system of claim 1, wherein in-between each of a plurality of separate instances of the HV signal generator being used to produce the HV tissue treatment signal that is delivered to the patient tissue during the treatment procedure, the controller is configured to:

cause the LV signal generator to be used to produce the LV tissue impedance measurement signal that is delivered to the patient tissue;

produce an updated estimate of the impedance of the patient tissue based on the voltage of the LV tissue impedance measurement signal that is delivered to the patient tissue and based on an updated measure of the current that is delivered to the patient tissue, as measured using the current sense circuit; and adjust the voltage of the HV tissue treatment signal that is produced using the HV signal generator, in response to the updated estimate of the impedance of the patient tissue differing from an immediately preceding estimate of the impedance of the patient tissue, so that when the HV tissue treatment signal is next delivered to the patient tissue the patient tissue is treated with a further current that is approximately equal to the predetermined target current that was specified prior to beginning the treatment procedure.

3. The tissue treatment system of claim 1, wherein:

the LV signal generator includes a LV power supply; and the HV signal generator includes a HV power supply that is distinct from the LV power supply of the LV signal generator.

4. The tissue treatment system of claim 3, wherein:

the LV signal generator includes a LV waveform shaping circuit coupled between the LV power supply and the active and the return electrodes; and the HV signal generator includes a HV waveform shaping circuit, which is distinct from the LV waveform shaping circuit, and is coupled between the HV power supply and the active and the return electrodes.

5. The tissue treatment system of claim 3, wherein:

the LV signal generator and the HV signal generator share a same waveform shaping circuit.

6. The tissue treatment system of claim 1, wherein:

the current sense circuit comprises a LV current sense circuit configured to measure the current that is delivered to the patient tissue via the active electrode while the LV tissue impedance measurement signal, which is produced using the LV signal generator, is delivered to the patient tissue; and further comprising a HV current sense circuit, which is distinct from the LV current sense circuit, and is configured to measure a further current that is delivered to the patient tissue via the active electrode while the HV tissue treatment signal, which is produced using the HV signal generator, is delivered to the patient tissue;

wherein a resolution of measurements produced by the LV current sense circuit is tailored to a range of expected LV current measurements, and a resolution of measurements produced by the HV current sense circuit is tailored to a range of expected HV current measurements that differs from the range of expected LV current measurements.

7. The tissue treatment system of claim 6, wherein the controller is further configured to:

produce the estimate of the impedance of the patient tissue based on the voltage of the LV tissue impedance measurement signal that is delivered to the patient tissue and based on the current measured by the LV current sense circuit;

set a voltage of the HV tissue treatment signal, which is produced using the HV signal generator, based on the estimate of the impedance of the patient tissue; and adjust the voltage of the HV tissue treatment signal, which is produced using the HV signal generator, based on the further current measured by the HV current sense circuit.

8. A tissue treatment system that is configured to deliver a predetermined target current to patient tissue during a treatment procedure, wherein the predetermined target current comprises a default target current specified prior to beginning the treatment procedure or is specified by a clinician using a user interface of the tissue treatment system prior to beginning the treatment procedure, the tissue treatment system comprising:

a pair of electrodes including an active electrode and a return electrode;

a plurality of capacitors;

a power supply configured to charge the plurality of capacitors;

a waveform shaping circuit coupled between the plurality of capacitors and the pair of electrodes;

a current sense circuit configured to measure a current that is delivered to the patient tissue via the active electrode while a low voltage (LV) tissue impedance measurement signal is delivered to the patient tissue; and a controller configured to cause a first subset of the plurality of capacitors to be coupled to the waveform shaping circuit during a first period of time during which the LV tissue impedance measurement signal is to be delivered to patient tissue via the pair of electrodes;

cause a second subset of the plurality of capacitors to be coupled to the waveform shaping circuit during a second period of time during which a high voltage (HV) tissue treatment signal is to be delivered to the patient tissue via the pair of electrodes;

produce an estimate of an impedance of the patient tissue based on a voltage of the LV tissue impedance measurement signal that is delivered to the patient tissue and based on the current measured by the current sense circuit; and adjust a voltage of the HV tissue treatment signal during the treatment procedure, based on the estimate of the impedance of the patient tissue and one or more updates thereto, so that when the HV tissue treatment signal is delivered to the patient tissue during the treatment procedure the patient tissue is treated with a current that is approximately equal to the predetermined target current that was specified prior to beginning the treatment procedure;

wherein the voltage of the HV tissue treatment signal is at least five times greater than the voltage of the LV tissue impedance measurement signal;

the first subset of the plurality of capacitors includes at least one of the plurality of capacitors; and the second subset of the plurality of capacitors includes at least one of the plurality of capacitors and differs from the first subset of the plurality of capacitors.

9. The tissue treatment system of claim 8, wherein:

the power supply, the waveform shaping circuit, and the first subset of the plurality of capacitors are components of a LV signal generator configured to produce the LV tissue impedance measurement signal;

the power supply, the waveform shaping circuit, and the second subset of the plurality of capacitors are components of a HV signal generator configured to produce the HV tissue treatment signal; and the power supply and the waveform shaping circuit are shared by both the LV signal generator and the HV signal generator.

10. The tissue treatment system of claim 9, wherein in-between each of a plurality of separate instances of the HV tissue treatment signal being produced and delivered to the patient tissue during the treatment procedure, the controller is configured to:

produce an updated estimate of the impedance of the patient tissue; and adjust the voltage of the HV tissue treatment signal that is produced, in response to the updated estimate of the impedance of the patient tissue differing from an immediately preceding estimate of the impedance of the patient tissue, so that when the HV tissue treatment signal is next delivered to the patient tissue the patient tissue is treated with a further current that is approximately equal to the predetermined target current that was specified prior to beginning the treatment procedure.

11. A method for delivering a predetermined target current to patient tissue during a treatment procedure, wherein the predetermined target current comprises a default target current specified prior to beginning the treatment procedure or is specified by a clinician using a user interface prior to beginning the treatment procedure, the method comprising:

(a) producing a low voltage (LV) tissue impedance measurement signal and delivering the LV tissue impedance measurement signal to patient tissue via an active electrode and a return electrode;

(b) measuring a current that is delivered to the patient tissue via the active electrode while the LV tissue impedance measurement signal is delivered to the patient tissue;

(c) producing an estimate of an impedance of the patient tissue based on a voltage of the LV tissue impedance measurement signal that is delivered to the patient tissue and based on the current that is measured; and (d) producing a high voltage (HV) tissue treatment signal and delivering the HV tissue treatment signal via the active and return electrodes, wherein a voltage of the HV tissue treatment signal is at least five times greater than the voltage of the LV tissue impedance measurement signal, and wherein the producing the HV tissue treatment signal includes adjusting the voltage of the HV tissue treatment signal during the treatment procedure based on the estimate of the impedance of the patient tissue and one or more updates thereto so that when the HV tissue treatment signal is delivered to the patient tissue during the treatment procedure the patient tissue is treated with a current that is approximately equal to the predetermined target current that was specified prior to beginning the treatment procedure.

12. The method of claim 11, wherein steps (a), (b), (c) and (d) are performed in that order, and after being performed in that order, are repeated in that order such that when step (c) is repeated an updated estimate of the impedance of the patient tissue is produced, and such that when step (d) is repeated the voltage of the HV tissue treatment signal is controlled based on the updated estimate of the impedance of the patient tissue so that the patient tissue is treated with a further current that is approximately equal to the predetermined target current.

13. The method of claim 11, wherein steps (a), (b), (c) and (d) are performed in that order, and after being performed in that order, steps (a), (b) and (c) are repeated in that order to produce an updated estimate of the impedance of the patient tissue, and the method further comprising:

determining, based on the updated estimate of the impedance of the patient tissue, whether treatment of the patient tissue was sufficient or whether additional treatment of the patient tissue should be performed at an additional instance of step (d).

14. The method of claim 13, wherein when the additional treatment of the patient tissue is to be performed at the additional instance of step (d), then the producing the HV treatment signal at the additional instance of step (d) includes controlling the voltage of the HV tissue treatment signal based on the updated estimate of the impedance of the patient tissue so that the patient tissue is treated with a further current that is approximately equal to the predetermined target current.

15. The method of claim 11, wherein:

the producing the LV tissue impedance measurement signal at step (a) is performed using a LV signal generator; and the producing the HV tissue treatment signal at step (c) is performed using a HV signal generator that is distinct from the LV signal generator.

16. The method of claim 11, further comprising:

using a power supply to charge a plurality of capacitors;

using a waveform shaping circuit, coupled between the plurality of capacitors and the active and return electrodes, to shape the LV tissue impedance measurement signal and the HV tissue treatment signal;

wherein the producing and the delivering the LV tissue impedance measurement signal at step (a) includes coupling a first subset of the plurality of capacitors to the waveform shaping circuit during a first period of time;

the producing and the delivering the HV tissue treatment signal at step (c) includes coupling a second subset of the plurality of capacitors to the waveform shaping circuit during a second period of time;

the first subset of the plurality of capacitors includes at least one of the plurality of capacitors; and the second subset of the plurality of capacitors includes at least one of the plurality of capacitors and differs from the first subset of the plurality of capacitors.

17. A tissue treatment system that is configured to deliver a predetermined target current to patient tissue during a treatment procedure, wherein the predetermined target current comprises a default target current specified prior to beginning the treatment procedure or is specified by a clinician using a user interface of the tissue treatment system prior to beginning the treatment procedure, the tissue treatment system comprising:

one or more voltage signal generators;

a current sense circuit configured to measure a current that is delivered to the patient tissue via an active electrode while one of the one or more voltage signal generators is delivering a voltage signal to the patient tissue; and a controller configured to produce an estimate of an impedance of the patient tissue based on the current measured by the current sense circuit; and adjust a voltage of the voltage signal produced during the treatment procedure using one of the one or more voltage signal generators, based on the estimate of the impedance of the patient tissue, so that during the treatment procedure the patient tissue is treated with a current that is approximately equal to the predetermined target current that was specified prior to beginning the treatment procedure.

* * * * *